United States Patent
Kawai et al.

(10) Patent No.: US 6,915,230 B2
(45) Date of Patent: Jul. 5, 2005

(54) METHOD OF ESTIMATING FLOOR REACTIONS OF BIPEDAL WALKING BODY, AND METHOD OF ESTIMATING JOINT MOMENTS OF BIPEDAL WALKING BODY

(75) Inventors: Masakazu Kawai, Wako (JP); Yasushi Ikeuchi, Wako (JP); Hisashi Katoh, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/481,858

(22) PCT Filed: Jun. 27, 2002

(86) PCT No.: PCT/JP02/06467

§ 371 (c)(1),
(2), (4) Date: Dec. 22, 2003

(87) PCT Pub. No.: WO03/002309

PCT Pub. Date: Jan. 9, 2003

(65) Prior Publication Data

US 2004/0167641 A1 Aug. 26, 2004

Related U.S. Application Data

(60) Provisional application No. 60/300,815, filed on Jun. 27, 2001.

(30) Foreign Application Priority Data

Jul. 13, 2001 (JP) ........................................ 2001-214174
Feb. 15, 2002 (JP) ........................................ 2002-039201

(51) Int. Cl.[7] .............................................. G06F 15/00
(52) U.S. Cl. ...................................... 702/139; 702/127
(58) Field of Search ..................... 180/8.1, 8.6; 73/172, 73/862.381; 318/560, 567, 568.1, 568.11, 568.12, 568.16; 702/33, 41, 127, 138, 139, 141

(56) References Cited

U.S. PATENT DOCUMENTS

| | | | | |
|---|---|---|---|---|
| 5,151,859 A | * | 9/1992 | Yoshino et al. | ................ 701/23 |
| 5,221,883 A | * | 6/1993 | Takenaka et al. | ...... 318/568.12 |
| 5,343,397 A | * | 8/1994 | Yoshino et al. | ................ 701/23 |
| 5,349,277 A | * | 9/1994 | Takahashi et al. | ..... 318/568.12 |
| 5,355,064 A | * | 10/1994 | Yoshino et al. | ........ 318/568.12 |

(Continued)

FOREIGN PATENT DOCUMENTS

| | | |
|---|---|---|
| EP | 1 120 203 A1 | 8/2001 |
| JP | 2000-249570 | 9/2000 |

OTHER PUBLICATIONS

, J; Dilworth, P; Pratt, G;"Virtual Model Control of a Bipedal Walking Robot"; Proceedings IEEE International Conference on Robotics and Automation; vol.: 1; Apr. 20–25, 1997; pp 193–198.*

(Continued)

*Primary Examiner*—John Barlow
*Assistant Examiner*—Douglas N Washburn
(74) *Attorney, Agent, or Firm*—Rankin, Hill, Porter & Clark LLP

(57) ABSTRACT

A method is presented for determination of single stance or double stance state of leg bodies of a bipedal mobile body (BMB). In a single stance state, a floor reaction force acting on a leg body touching the ground is estimated based on an equation of motion for the center of gravity (GO) of a BMB. In a double stance state, floor reaction forces, Fr and Ff respectively, acting on the leg bodies are estimated based on an equation of motion for GO of a BMB and an expression of relation between components of Fr and Ff on the respective leg bodies and positions of ankle portions of the leg bodies relative to the GO of the BMB. Further, based on an inverse dynamics model, knee and hip joint moments of each leg body are estimated using floor reaction force values.

9 Claims, 15 Drawing Sheets

U.S. PATENT DOCUMENTS

| | | | | |
|---|---|---|---|---|
| 5,357,433 A | * | 10/1994 | Takenaka et al. | 701/23 |
| 5,402,050 A | * | 3/1995 | Ozawa | 318/568.12 |
| 5,404,086 A | * | 4/1995 | Takenaka et al. | 318/568.12 |
| 5,416,393 A | * | 5/1995 | Gomi et al. | 318/568.2 |
| 5,426,586 A | * | 6/1995 | Ozawa | 701/23 |
| 5,432,417 A | * | 7/1995 | Takenaka et al. | 318/568.12 |
| 5,445,235 A | * | 8/1995 | Gomi et al. | 180/8.6 |
| 5,455,497 A | * | 10/1995 | Hirose et al. | 318/568.12 |
| 5,459,659 A | * | 10/1995 | Takenaka | 700/260 |
| 5,513,106 A | * | 4/1996 | Yoshino et al. | 701/23 |
| 5,737,217 A | * | 4/1998 | Nishikawa et al. | 700/56 |
| 5,739,655 A | * | 4/1998 | Torii et al. | 318/568.12 |
| 5,808,433 A | * | 9/1998 | Tagami et al. | 318/568.12 |
| 5,838,130 A | * | 11/1998 | Ozawa | 318/568.2 |
| 5,872,893 A | * | 2/1999 | Takenaka et al. | 700/245 |
| 5,936,367 A | * | 8/1999 | Takenaka | 318/568.12 |
| 6,243,623 B1 | * | 6/2001 | Takenaka et al. | 700/245 |
| 6,266,576 B1 | * | 7/2001 | Okada et al. | 700/245 |
| 6,289,265 B1 | * | 9/2001 | Takenaka et al. | 700/245 |
| 6,301,524 B1 | * | 10/2001 | Takenaka | 700/245 |
| 6,463,356 B1 | * | 10/2002 | Hattori et al. | 700/245 |
| 6,472,838 B1 | * | 10/2002 | Shikazono et al. | 318/567 |
| 6,479,960 B2 | * | 11/2002 | Nakai et al. | 318/569 |
| 6,480,761 B2 | * | 11/2002 | Ueno et al. | 700/245 |
| 6,564,888 B1 | * | 5/2003 | Gomi et al. | 180/8.6 |
| 6,580,969 B1 | * | 6/2003 | Ishida et al. | 700/245 |
| 6,640,160 B2 | * | 10/2003 | Takahashi et al. | 700/245 |
| 2004/0133308 A1 | * | 7/2004 | Kato et al. | 700/245 |
| 2004/0181312 A1 | * | 9/2004 | Miura et al. | 700/258 |
| 2004/0206164 A1 | * | 10/2004 | Kawai et al. | 73/65.07 |

OTHER PUBLICATIONS

Hu; Pratt, J; Pratt, G; "Adaptive dynamic control of a bipedal walking robot with radial basis function neural networks"; Proceedings IEEE/RSJ International Conference on Intelligent Robots and Systems, 1998; vol.: 1; Oct. 13–17, 1998; pp 400 405.*

Jianjuen Hu; Pratt, J; Chee–Meng Chew; Herr, H; Pratt, G; "Adaptive virtual model control of a bipedal walking robot"; Proceedings., IEEE International Joint Symposia on Intelligence and Systems; May 21–23, 1998; pp 245–251.*

Pratt, J.; Pratt, G.; "Intuitive control of a planar bipedal walking robot"; Proceedings IEEE International Conference on Robotics and Automation; vol.: 3, May 16–20, 1998; pp 2014–2021.*

Fujimoto, Y; Kawamura, A; "Simulation of an autonomous biped walking robot including environmental force interaction"; IEEE Robotics & Automation Magazine; vol.: 5, Issue: 2; Jun. 1998; pp 33–42.*

Fujimoto, Y; Obata, S; Kawamura, A; "Robust biped walking with active interactive control between foot and ground"; Proceedings IEEE International Conference on Robotics and Automation; vol.: 3; May 16–20, 1998 ; pp 2030–2035.*

Gorce, P; "Dynamic control of bipeds using postural adjustment strategy"; IEEE International Conference on Systems, Man, an Cybernetics; vol.: 1; Oct. 12–15, 1997; pp 453–458.*

Gorce, P; "Dynamic postural control method for biped in unknown environment"; IEEE Transactions on Systems, Man and Cybernetics, Part A; vol.: 29 , Issue: 6; Nov. 1999; pp 616–626.*

Van Der Linde, R; "Active leg compliance for passive walking"; Proceedings IEEE International Conference on Robotics and Automation; vol. 3; May 16–20, 1998; pp 2339–2344.*

Ching–Long Shih; Chien–Jung Chiou; "The motion control of a statically stable biped robot on an uneven floor"; IEEE Transactions on Systems, Man and Cybernetics, Part B; vol.: 28 , Issue: 2; Apr. 1998; pp 244–249.*

Shih, C; Gruver, W; "Control of a biped robot in the double–support phase"; IEEE Transactions on Systems, Man and Cybernetics; vol.: 22 , Issue: 4; Jul.–Aug. 1992; pp 729–735.*

Zohdy, M; Zaher, A; "Robust control of biped robots"; Proceedings of the American Control Conference; vol.: 3; Jun. 28–30, 2000; pp 1473–1477.*

Silva, F; Machado, J; "Position/force control of biped walking robots"; IEEE International Conference on Systems, Man, and Cybernetics; vol.: 5; Oct. 8–11, 2000; pp 3288–3293.*

Larin, V; "Control of walking machine"; Proceedings of the IEEE Intelligent Vehicles Symposium; Oct. 3–5, 2000; pp 626–631.*

Shibata, M; Natori, T; "Impact force reduction for biped robot based on decoupling COG control scheme"; Proceedings 6th International Workshop on Advanced Motion Control; Mar. 30–Apr. 1, 2000; pp 612–617.*

Lim, H; Takanishi, A; "A Waseda biped humanoid robots realizing human–like motion"; Proceedings 6th International Workshop o Advanced Motion Control; Mar. 30–Apr. 1, 2000; pp 525–530.*

Espiau, B; Sardain, P; "The anthropomorphic biped robot BIP2000"; Proceedings ICRA '00. IEEE International Conference on Robotics and Automation; vol.: 4; Apr. 24–28, 2000; pp 3996–4001.*

Perrin, B; Chevallereau, C; Verdier, C; "Calculation of the direct dynamic model of walking robots: comparison between two methods"; Proceedings IEEE International Conference on Robotics and Automation; vol.: 2; Apr. 20–25, 1997; pp 1088–109.*

Sonoda, N.; Murakami, T.; Ohnishi, K.; "An approach to biped robot control utilized redundancy in double support phase"; 23rd International Conference on Industrial Electronics, Control and Instrumentation; vol.: 3; Nov. 9–14, 1997; pp 1332–1336.*

Guanzheng Tan; Peng Zhang; "A new method for computing key dynamic parameters of dynamic walking of biped robots"; IEE International Conference on Intelligent Processing Systems; vol.: 2; Oct. 28–31, 1997; pp 1292–1296.*

Fujimoto, Y; Kawanura, A; "Biped walking control with optimal foot force distribution by quadratic programming"; IEEE/ASME International Conference on Advanced Intelligent Mechatronics; Jun. 16–20, 1997; pp 108.*

Guihard, M; Gorce, P; "A new way to tackle position/force control for pneumatic robots"; Proceedings of the 1996 IEEE/RSJ International Conference on Intelligent Robots and Systems; vol.: 2; Nov. 4–8, 1996; pp 603–610.*

Meng Yue; Mark Minor; Ning Xi; Mukherjee, R; "Kinematic workspace analyses of a miniature walking robot"; Proceedings. 199 IEEE/RSJ International Conference on Intelligent Robots and Systems; vol.: 3; Oct. 17–21, 1999; pp 1798–1803.*

Qiang Huang; Kajita, S; Koyachi, N; Kaneko, K.; Yokoi, K; Arai, H; Komoriya, K; Tanie, K; "A high stability, smooth walking pattern for a biped robot"; IEEE International Conference on Robotics and Automation; vol.: 1; May 10–15, 1999; pp 65–71.*

Goswami, A; "Foot rotation indicator (FRI) point: a new gait planning tool to evaluate postural stability of biped robots"; Proceedings 1999 IEEE International Conference on Robotics and Automation; vol.: 1; May 10–15, 1999; pp 47–52.*

Fujimoto, Y; Kawamura, A; "Attitude control experiments of biped walking robot based on environmental force interaction"; 5th International Workshop on Advanced Motion Control; Jun. 29–Jul. 1, 1998; pp 70–75.*

Ono, T; Murakami, T; Ohnishi, K; "An approach to biped robot control according to surface condition of ground"; 5th Internation Workshop on Advanced Motion Control; Jun. 29–Jul. 1, 1998; pp 129–134.*

Gorce, P; Vanel, O; Ribreau, C; "Equilibrium study of "human" robot"; IEEE International Conference on Systems, Man and Cybernetics, 'Intelligent Systems for the 21st Century'; vol.: 2; Oct. 22–25, 1995; pp 1309–1314.*

Mitobe, K; Mori, N; Aida, K; Nasu, Y; "Nonlinear feedback control of a biped walking robot"; Proceedings IEEE International Conference on Robotics and Automation; vol.: 3; May 21–27, 1995; pp 2865–2870.*

Dunn, E; Howe, R; "Towards smooth bipedal walking"; Proceedings IEEE International Conference on Robotics and Automatio May 8–13, 1994; pp 2489–2494.*

Sano, A; Furusho, J; "Control of torque distribution for the BLR–G2biped robot"; Fifth International Conference on Advanced Robotics, 'Robots in Unstructured Environments'; Jun. 19–22, 1991; pp 729–734.*

Lieh, J; "Computer–aided modeling and control of multi-body systems for robotics application"; Proccedings IEEE International Conference on Robotics and Automation; Apr. 9–11, 1991; pp 2385–2390.*

* cited by examiner

METHOD OF ESTIMATING FLOOR REACTIONS OF BIPEDAL WALKING BODY, AND METHOD OF ESTIMATING JOINT MOMENTS OF BIPEDAL WALKING BODY

TECHNICAL FIELD

The present invention relates to a method of estimating floor reaction forces acting on leg bodies of a bipedal walking moving body such as a human being or a bipedal walking robot, and further relates to a method of estimating moments acting on joints of the leg bodies of the bipedal walking moving body by the use of estimated values of the floor reaction forces.

BACKGROUND ART

For example, when executing an operation control of a walking assist device assisting walking motions of a human being, or a control of moving motions of a bipedal walking robot, it becomes necessary to successively grasp floor reaction forces acting on leg bodies (specifically, forces acting on ground touching portions of the leg bodies from a floor) of the human being or the bipedal walking robot. By grasping the floor reaction forces, it becomes possible to grasp moments or the like acting on joints of the leg bodies of the bipedal walking moving body and, based on the grasped moments or the like, it becomes possible to determine desired assist forces of the walking assist device, or desired driving torques for the respective joints of the bipedal walking robot or the like.

As a technique of grasping the foregoing floor reaction forces, there has been known one disclosed in, for example, Laid-open Unexamined Patent Publication No. 2000-249570. According to this technique, in view of the fact that a waveform of temporal variation in floor reaction force on each leg body periodically changes during steady walking of a bipedal walking moving body, the floor reaction force on each leg body is grasped as a composite value (linear combination) of a plurality of trigonometric functions having mutually different periods being 1/n (n=1, 2, . . . ) of a walking period. In this case, as a weighting coefficient of each trigonometric function upon combining the plurality of trigonometric functions, there has been used a prescribed value determined in advance per bipedal walking moving body, or a value obtained by adjusting it depending on topography.

However, inasmuch as the foregoing technique aims to grasp the floor reaction forces on the leg bodies with respect to one step or a plurality of steps of the bipedal walking moving body, when a gait of the bipedal walking moving body changes in sequence, it is difficult to accurately grasp the floor reaction forces. Further, for enhancing the accuracy of the floor reaction forces to be grasped, it is necessary to set the foregoing weighting coefficients of the trigonometric functions per bipedal walking moving body, or adjust them depending on topography or the like. Therefore, it is difficult to accurately grasp the floor reaction forces with a reduced influence of environment for movement of the bipedal walking moving body or a difference in individuality of the bipedal walking moving body.

In case of a bipedal walking robot, for example, there has been known one wherein force sensors such as six-axis force sensors are attached to ankle portions or foot portions of respective leg bodies, and floor reaction forces are grasped by outputs of these force sensors. Further, there has also been known a technique of walking a bipedal walking moving body on a force plate placed on a floor, and grasping floor reaction forces by outputs of the force plate.

However, the technique using the force sensors has a disadvantage that when grasping floor reaction forces on leg bodies of particularly a human being, inasmuch as the force sensors should be attached to ankle portions or foot portions of the human being, the force sensors become obstructive to the walking in an ordinary living environment. Further, in case of the one using the force plate, the floor reaction forces can only be grasped in an environment where the force plate is arranged.

The present invention has been made in view of the foregoing background and has an object to provide a floor reaction force estimating method that can accurately grasp floor reaction forces in real time with a relatively simple technique, and that is suitable for grasping floor reaction forces with respect to particularly a human being as a bipedal walking moving body.

Further, it is an object thereof to provide a method of estimating joint moments of the bipedal walking moving body, which can accurately grasp in real time the moments acting on joints such as knee joints of leg bodies by the use of estimated values of the floor reaction forces.

DISCLOSURE OF THE INVENTION

At the outset, explanation will be given about a basic way of thinking about a floor reaction force estimating method of a bipedal walking moving body according to the present invention.

As motion states of leg bodies of a bipedal walking moving body, for example, as motion states of the leg bodies upon walking, there are a single stance state wherein, as illustrated in FIG. 1(a), only one leg body 2 (a leg body on a front side in an advancing direction in the figure) of both leg bodies 2, 2 of a bipedal walking moving body 1 touches the ground, and a double stance state wherein both leg bodies 2, 2 touch the ground as shown in FIG. 1(b).

Here, first, in the foregoing single stance state, an equation of motion for the center of gravity (specifically, an equation of motion about translation of the center of gravity) of the bipedal walking moving body in an absolute coordinate system fixed relative to the ground on which the bipedal walking moving body moves is given by an expression of relation such that the product of an acceleration of the center of gravity and a weight of the bipedal walking moving body is equal to a resultant force of gravity acting on the center of gravity (=the weight of the bipedal walking moving body× the acceleration of gravity) and a floor reaction force acting from the floor on a ground touching portion of the leg body touching the ground. Specifically, as shown in FIG. 1(a), for example, in an absolute coordinate system Cf fixed relative to a floor A, given that components of an acceleration a of the center of gravity G0 of the bipedal walking moving body 1 in an X-axis direction (horizontal direction in the advancing direction of the bipedal walking moving body 1) and a Z-axis direction (vertical direction) are ax and az, respectively, and components of a floor reaction force F on the leg body 2 (leg body 2 on the supporting leg side) touching the ground in the X-axis direction and the Z-axis direction are Fx and Fz, respectively, the equation of motion for the center of gravity G0 is expressed by the following equation (1).

$$^T(Fx,\ Fz-M\cdot g) = M\cdot{}^T(ax,\ az) \tag{1}$$

(wherein M: weight of bipedal walking moving body, and g: acceleration of gravity)

Parenthesis portions $^T(\,,\,)$ on both sides in the equation (1) represent two-component vectors. In the present specification, the notation in the form of $^T(\,,\,)$ represents a vector.

Therefore, if the acceleration $a={}^T(ax, az)$ of the center of gravity G0 of the bipedal walking moving body 1 is grasped, an estimated value of the floor reaction force $F={}^T(Fx, Fz)$ can be derived by the following equation (2) using the acceleration a, a value of the weight M of the bipedal walking moving body 1, and a value of the acceleration of gravity g.

$$^T(Fx, Fz) = M \cdot {}^T(ax, az-g) \quad (2)$$

In this case, the weight M necessary for deriving the estimated value of the floor reaction force F can be grasped in advance by measurement or the like. Further, with respect to a position of the center of gravity G0 and the acceleration a, it is possible to grasp them in sequence according to a known technique or the like using outputs of sensors such as sensors for detecting bending angles (rotation angles) of the respective joints of the bipedal walking moving body 1, accelerometers, gyro sensors, and so forth, which will be described later in detail.

Next, an equation of motion for the center of gravity (specifically, an equation of motion about translation of the center of gravity) of the bipedal walking moving body in the foregoing both-leg ground touching state is given by an expression of relation such that the product of an acceleration of the center of gravity and the weight of the bipedal walking moving body is equal to a resultant force of gravity acting on the center of gravity (=the weight of the bipedal walking moving body×the acceleration of gravity) and floor reaction forces acting from the floor on the respective ground touching portions of both leg bodies (two floor reaction forces corresponding to both leg bodies, respectively). Specifically, as shown in FIG. 1(b), given that X and Z coordinate components of a floor reaction force Ff on the leg body 2 on the front side in the advancing direction of the bipedal walking moving body 1 are Ffx and Ffz, and X and Z coordinate components of a floor reaction force Fr on the leg body 2 on the rear side are Frx and Frz, the equation of motion for the center of gravity G0 is expressed by the following equation (3).

$$^T(Ffx+Frx, Ffz+Frz-M \cdot g) = M \cdot {}^T(ax, az) \quad (3)$$

The meaning of ax, az, M, and g in the equation (3) is as described before.

On the other hand, according to knowledge of the inventors of the present application, in the double stance state, the floor reaction forces Ff, Fr respectively relating to the leg bodies 2, 2 can be deemed to almost act from specific portions 12f, 12r (e.g. ankle portions) in the vicinity of lower end portions of the respective leg bodies 2, 2 toward the center of gravity G0 of the bipedal walking moving body 1, as shown in FIG. 1(b). Then, there is established an expression of certain relation between a position of the specific portion 12f, 12r of the leg body 2 relative to the center of gravity G0, and the floor reaction force Ff, Fr acting on the leg body 2, that is, an expression of relation representing a relation wherein a direction of a segment connecting between the center of gravity G0 and the specific portion 12f, 12r of the leg body 2 (a direction of a position vector of the specific portion 12f, 12r relative to the center of gravity G0) is the same as a direction of the floor reaction force Ff, Fr relating to the leg body 2.

Specifically, referring to FIG. 1(b), given that coordinates of a position of the center of gravity G0 in the foregoing absolute coordinate system Cf are (Xg, Zg), coordinates of a position of the specific portion 12f of the front-side leg body 2 are (Xf, Zf), and coordinates of a position of the specific portion 12r of the rear-side leg body 2 are (Xr, Zr), the foregoing expressions of relation become the following equations (4).

$$(Zf-Zg)/(Xf-Xg)=Ffz/Ffx$$

$$(Zr-Zg)/(Xr-Xg)=Frz/Frx \quad (4)$$

Then, the following equations (5) are obtained from these equations (4) and the foregoing equation (3).

$$Ffx = M \cdot \{\Delta Xf \cdot (\Delta Zr \cdot ax - \Delta Xr \cdot az - \Delta Xr \cdot g)\} / (\Delta Xf \cdot \Delta Zr - \Delta Xr \cdot \Delta Zf) \quad (5)$$

$$Ffz = M \cdot \{\Delta Zf \cdot (\Delta Zr \cdot ax - \Delta Xr \cdot az - \Delta Xr \cdot g)\} / (\Delta Xf \cdot \Delta Zr - \Delta Xr \cdot \Delta Zf)$$

$$Frx = M \cdot \{\Delta Xr \cdot (-\Delta Zf \cdot ax + \Delta Xf \cdot az + \Delta Xf \cdot g)\} / (\Delta Xf \cdot \Delta Zr - \Delta Xr \cdot \Delta Zf)$$

$$Frz = M \cdot \{\Delta Zr \cdot (-\Delta Zf \cdot ax + \Delta Xf \cdot az + \Delta Xf \cdot g)\} / (\Delta Xf \cdot \Delta Zr - \Delta Xr \cdot \Delta Zf)$$

(wherein $\Delta Zf=Xf-Xg$, $\Delta Zf=Zf-Zg$, $\Delta Xr=Xr-Xg$, and $\Delta Zr=Zr-Zg$)

Therefore, if an acceleration $a={}^T(ax, az)$ of the center of gravity G0 of the bipedal walking moving body 1 is grasped, and positions (these are expressed by $\Delta Xf$, $\Delta Zf$, $\Delta Xr$, and $\Delta Zr$ in the equations (5)) of the specific portions 12f, 12r respectively of the leg bodies 2, 2 relative to the center of gravity G0 of the bipedal walking moving body 1 are grasped, estimated values of the floor reaction forces $Ff={}^T(Ffx, Ffz)$, $Fr={}^T(Frx, Frz)$ on the respective leg bodies 2, 2 can be obtained by the foregoing equations (5) using a value of the weight M and a value of the acceleration of gravity g of the bipedal walking moving body 1 and the grasped acceleration a and the positions of the specific positions 12f, 12r.

In this case, the weight M necessary for obtaining the estimated values of the floor reaction forces Ff, Fr can be grasped in advance by measurement or the like. With respect to the acceleration a of the center of gravity G0, the position of the center of gravity G0, and the positions of the specific portions 12f, 12r relative to the center of gravity G0, although details will be described later, it is possible to grasp them in sequence by a known technique or the like using outputs of the sensors detecting bending angles (rotation angles) of the respective joints of the bipedal walking moving body 1, the accelerometers, the gyro sensors, and so forth.

The present invention will be described next on the basis of what has been explained above. For accomplishing the foregoing objects, a method of estimating a floor reaction force for a bipedal walking moving body according to the present invention, i.e. a method of estimating a floor reaction force acting on each leg body of a bipedal walking moving body, comprises a first step of judging whether a motion state of the leg bodies of said bipedal walking moving body is a single stance state in which only one of the leg bodies touches the ground, or a double stance state in which both leg bodies touch the ground; a second step of sequentially deriving positions of the center of gravity of said bipedal walking moving body, and sequentially deriving accelerations of said center of gravity in an absolute coordinate system fixed relative to the ground by the use of time series data about the positions of said center of gravity; and a third step of sequentially deriving positions of a specific portion relative to said center of gravity at least in said double stance state, said specific portion predetermined in the neighborhood of a lower end portion of each leg body. Then, the method of estimating a floor reaction force of the present invention is characterized by further comprising a step of deriving estimated values of said floor reaction force acting on the leg body touching the ground sequentially, in the single stance state of said bipedal walking moving body, based on an equation of motion for said center of gravity expressed by a weight and an acceleration of gravity of the bipedal walking moving body, the acceleration of said center of gravity, and said floor reaction force acting on the leg body touching the ground; and a step of deriving estimated values of said floor reaction forces respectively acting on both leg bodies sequentially, in the double stance state of said bipedal walking moving body, based on an equation of motion for said center of gravity expressed by a weight and an acceleration of gravity of the bipedal walking moving body, the acceleration of said center of gravity, and said floor reaction forces respectively acting on both leg bodies, and an expression of relation between the position of said specific portion of each leg body relative to said center of gravity and said floor reaction force acting on said leg body, said expression of relation being determined based on assumption that said floor reaction force acting on each leg body acts from said specific portion of said leg body toward said center of gravity.

According to the present invention as described above, in the foregoing first step, it is judged whether the motion state of the leg bodies of the bipedal walking moving body is the single stance state or the double stance state, and the estimated values of the foregoing floor reaction forces are derived by the techniques depending on the respective supporting states. Specifically, in the single stance state of the bipedal walking moving body, the estimated value of the foregoing floor reaction force acting on the leg body touching the ground is derived from values of the weight, the acceleration of gravity, and the acceleration of the center of gravity of the bipedal walking moving body (see the equation (2)) based on the foregoing equation of motion for the center of gravity of the bipedal walking moving body (see the equation (1)).

On the other hand, in the double stance state of the bipedal walking moving body, the estimated values of the floor reaction forces acting on both leg bodies, respectively, are derived from the weight, the acceleration of gravity, and the acceleration of the center of gravity of the bipedal walking moving body, and the position of the specific portion of each leg body relative to the center of gravity (see the equations (5)) based on the foregoing equation of motion for the center of gravity of the bipedal walking moving body (see the equation (3)) and the expression of relation (the equation (4)) between the position of the specific portion of each leg body relative to the foregoing center of gravity, and the foregoing floor reaction force acting on the subject leg body. Incidentally, in the single stance state, the floor reaction force acting on the free-leg side leg body (the leg body not touching the ground) is "0".

In this case, the weight of the bipedal walking moving body necessary for deriving the estimated value of the floor reaction force may be grasped in advance by measurement or the like. With respect to the position of the center of gravity and the acceleration of the bipedal walking moving body, and the position of the specific portion of each leg body relative to the center of gravity, it is possible to grasp them in real time using data about outputs of sensors that are relatively small in size and easy to be attached to the bipedal walking moving body, such as sensors (potentiometers or the like) detecting bending angles (rotation angles) of the respective joints of the bipedal walking moving body, accelerometers, gyro sensors, and so forth.

Therefore, according to the method of estimating a floor reaction force of the present invention, it is possible to grasp the floor reaction forces in real time by the relatively simple technique without attaching force sensors to ankle portions or foot portions of the bipedal walking moving body, or using a force place.

In the method of estimating a floor reaction force of the present invention as described above, it is preferable that the specific portion of each leg body is an ankle portion of the leg body. Thereby, particularly, reliability of the foregoing assumption in the both-leg ground touching state is enhanced. Therefore, the accuracy of not only the estimated value of the floor reaction force in the foregoing single stance state, but also the estimated values of the floor reaction forces in the double stance state can be enhanced. That is, the floor reaction force can be accurately estimated irrespective of the motion state of the leg bodies.

Further, the method of estimating a floor reaction force of the present invention comprises a step of measuring an acceleration, in an upward/downward direction, of a lower portion of a body supported on both leg bodies via a hip joint of each leg body, said lower portion of the body located near said hip joints, wherein, in said first step, the motion state of said bipedal walking moving body is judged such that when the acceleration of said lower portion of the body in the upward/downward direction increases to a predetermined threshold value or more, said double stance state starts while said single stance state finishes and, when the estimated value of said floor reaction force acting on the leg body which precedingly makes a takeoff is lowered to a predetermined threshold value or less in said double stance state, said double stance state finishes while said single stance state starts.

Specifically, upon transition of the motion state of the leg bodies from the single stance state to the double stance state during movement (walking) of the bipedal walking moving body, landing of the free-leg side leg body causes the acceleration of a lower part of a body in an upward/downward direction (upward acceleration) to temporarily become remarkably large. This phenomenon is not generated normally in the other motion state of the leg bodies. On the other hand, upon transition of the motion state of the leg bodies from the double stance state to the single stance state, a takeoff operation of one of the leg bodies causes the floor reaction force acting on that leg body to be lowered to "0". Therefore, by judging the motion state of the leg bodies as described above, judgement as to whether it is the single stance state or the double stance state can be properly carried out. As a result, a floor reaction force estimated value calculation method that differs between the single stance state and the double stance state can be switched at appropriate timing to thereby increase the accuracy of the estimated value of the floor reaction force. The acceleration, in the upward/downward direction, of the lower part of the body necessary for judging the motion state of the leg bodies can be easily grasped from an output of an accelerometer by, for example, attaching the accelerometer to the lower part of the body.

Like a human being, if the foregoing body has a waist coupled to both leg bodies via hip joints, and a chest located on the waist so as to be tilted freely relative to the waist, it is preferable that the acceleration, in the upward/downward direction, of the lower part of the body to be measured is an acceleration of the waist in the upward/downward direction.

Further, in the method of estimating a floor reaction force of the present invention, various techniques are considered as a technique of grasping the position of the center of gravity of the bipedal walking moving body and the acceleration of the center of gravity in the foregoing second step, and it is possible to use various known methods. However, it is preferable to grasp the position of the center of gravity and the acceleration of the center of gravity according to the following method.

Specifically, the method comprises a step of respectively measuring an inclination angle of a body supported on both leg bodies via a hip joint of each leg body, bending angles respectively of at least the hip joint and a knee joint of each leg body, and an acceleration of a predetermined reference point of said bipedal walking moving body in said absolute coordinate system, wherein, in said second step, based on the inclination angle of said body, the bending angles respectively of said hip joints and said knee joints, a rigid body link model formed by expressing said bipedal walking moving body as a linked body of a plurality of rigid bodies, prederived weights of respective rigid-body corresponding portions of the bipedal walking moving body corresponding to the respective rigid bodies of said rigid body link model, and positions of the prederived centers of gravity of the rigid-body corresponding portions in the respective rigid-body corresponding portions, positions of the center of gravity of said bipedal walking moving body relative to said reference point are sequentially derived, accelerations of said center of gravity relative to said reference point are sequentially derived based on time series data about the positions of said center of gravity, and the acceleration of said center of gravity in said absolute coordinate system is derived from the acceleration of said center of gravity relative to said reference point, and the acceleration of said reference point in said absolute coordinate system.

Specifically, when the reference point is arbitrarily set to the bipedal walking moving body, the position of the center of gravity of the bipedal walking moving body relative to the reference point is almost determined by a mutual posture relationship among the body, a thigh portion of each leg body from the hip joint to the knee joint, and a crus portion on a lower side below the knee joint. By measuring the inclination angle of the body and the bending angles respectively of the hip joints and the knee joints, the posture relationship can be grasped from those measurement data. Further, although details will be described later, when the foregoing rigid body link model is supposed for the bipedal walking moving body (e.g. a model regarding as rigid bodies a portion (including the body) on an upper side of the hip joints of both leg bodies of the bipedal walking moving body, and the thigh portion and the crus portion of each leg body), the position of the center of gravity of the bipedal walking moving body relative to the foregoing reference point can be derived based on the weights of the respective rigid-body corresponding portions of the bipedal walking moving body, the positions of the centers of gravity of the rigid-body corresponding portions in the respective rigid-body corresponding portions (specifically, the positions of the rigid-body corresponding portions in coordinate systems fixed to the respective rigid-body corresponding portions), and the foregoing posture relationship. Further, the acceleration of the center of gravity relative to the reference point can be derived as a second-order differentiated value of the position of the center of gravity which is grasped from time series data about the positions of the center of gravity. Therefore, by measuring the acceleration of the reference point in the foregoing absolute coordinate system, the acceleration of the center of gravity of the bipedal walking moving body in the absolute coordinate system can be derived as a composite acceleration of the acceleration of the center of gravity relative to the reference point and the acceleration of the reference point.

In this case, the inclination angles of the body necessary for grasping the acceleration of the bipedal walking moving body as described above can be grasped from outputs of accelerometers and gyro sensors, or inclinometers or the like attached to the body, and the bending angles of the hip joint and the knee joint of each leg body can be grasped from outputs of sensors such as potentiometers attached to the portions of the respective joints. Further, the acceleration of the reference point in the absolute coordinate system can be grasped from outputs of sensors such as accelerometers attached to a portion integral with the reference point. Further, the weights of the respective rigid-body corresponding portions of the bipedal walking moving body and the positions of the centers of gravity of the rigid-body corresponding portions in the respective rigid-body corresponding portions can be grasped in advance by measurement or the like.

Therefore, it becomes possible to easily grasp in real time the position and acceleration of the center of gravity of the bipedal walking moving body without mounting the relatively large sensors and so forth onto the bipedal walking moving body.

When deriving the position and acceleration of the center of gravity of the bipedal walking moving body as described above, it is preferable that the reference point is set to the body. Thereby, the sensors such as the accelerometers for measuring the acceleration of the reference point in the absolute coordinate system can be mounted on the body, and therefore, the sensors attached to the leg bodies can be reduced, thereby to make it possible to avoid the situation where those sensors become obstructive to walking motions of the bipedal walking moving body.

On the other hand, like a human being, if the body has a waist coupled to both leg bodies via hip joints, and a chest located on the waist so as to be tiltable relative to the waist, it is preferable that the inclination angle of the body used for deriving the position of the center of gravity comprises inclination angles respectively of the waist and the chest. Particularly in this case, it is preferable that the foregoing rigid body link model is a model expressing a crus portion located on a lower side of the knee joint of each leg body of the bipedal walking moving body, a thigh portion between the knee joint and the hip joint, the waist, and an upper body portion located on an upper side of the waist and including the chest, as rigid bodies, respectively.

In accordance therewith, particularly when the bipedal walking moving body is a human being, the position of the center of gravity thereof and the acceleration thereof can be grasped accurately to thereby enhance the accuracy of the estimated values of the floor reaction forces.

When deriving the position of the center of gravity of the bipedal walking moving body relative to the reference point based on the inclination angles of the body and so forth as described above, the position of the foregoing specific portion of each leg body relative to the center of gravity of the bipedal walking moving body can be derived by deriving the position of the specific portion relative to the reference point in the foregoing third step. In this case, parameters necessary for deriving the position of the specific portion relative to the reference point differ depending on a set position of the reference point. For example, when the specific portion is an ankle portion of each leg body, and the reference point is set to the body, it is possible to derive the position of the specific portion of each leg body relative to the reference point based on the inclination angle of the body (the inclination angle of the waist when the body has the waist and the chest, and the reference point is set to the waist), the bending angles of the hip joint and the knee joint of each leg body, and the sizes (lengths) of the thigh portion and the crus portion of each leg body.

Next, a method of estimating a moment for a bipedal walking moving body according to the present invention is a method of estimating a moment acting on at least one joint of each leg body of the bipedal walking moving body by the use of the estimated values of the floor reaction force on each leg body sequentially derived by the foregoing method of estimating a floor reaction force. Then, the method of estimating a moment of the present invention is characterized by comprising a step of respectively measuring an inclination angle of a body supported on both leg bodies via a hip joint of each leg body, bending angles respectively of at least the hip joint and a knee joint of each leg body, and an acceleration of a predetermined reference point of said bipedal walking moving body in said absolute coordinate system; a step of sequentially deriving inclination angles of respective rigid-body corresponding portions of the bipedal walking moving body corresponding to the respective rigid bodies of said rigid body link model, based on the inclination angle of said body, the bending angles respectively of said hip joint and said knee joint of each leg body, and a rigid body link model formed by expressing said bipedal walking moving body as a linked body of a plurality of rigid bodies; a step of sequentially deriving positions of the centers of gravity of the respective rigid-body corresponding portions relative to said reference point, based on the inclination angles of said respective rigid-body corresponding portions, prederived weights of the respective rigid-body corresponding portions, and positions of the prederived centers of gravity of the rigid-body corresponding portions in the respective rigid-body corresponding portions, and sequentially deriving accelerations of the centers of gravity of the respective rigid-body corresponding portions relative to said reference point based on time series data about the positions of the centers of gravity of the respective rigid-body corresponding portions; a step of sequentially deriving accelerations of the centers of gravity of the respective rigid-body corresponding portions in said absolute coordinate system from the accelerations of the centers of gravity of the respective rigid-body corresponding portions relative to said reference point, and the accelerations of said reference point in said absolute coordinate system; a step of sequentially deriving angular velocities of the respective rigid-body corresponding portions based on time series data about the inclination angles of the respective rigid-body corresponding portions; a step of sequentially deriving estimated positions of a floor reaction force acting point of each leg body in said bipedal walking moving body, based on at least one of an inclination angle of a thigh portion of said leg body and the bending angle of the knee joint of said leg body as the rigid-body corresponding portions of said bipedal walking moving body; and a step of estimating a moment acting on at least one of the joints of each leg body of said bipedal walking moving body based on an inverse dynamics model using the estimated value of said floor reaction force, the estimated position of said floor reaction force acting point, the accelerations of the centers of gravity of the respective rigid-body corresponding portions and the angular velocities of said rigid-body corresponding portions in said absolute coordinate system, the inclination angles of the respective rigid-body corresponding portions, the prederived weights and sizes of the respective rigid-body corresponding portions, the positions of the prederived centers of gravity of the rigid-body corresponding portions in the respective rigid-body corresponding portions, and prederived moments of inertia of the respective rigid-body corresponding portions.

When, as described before, the second step in the foregoing floor reaction force estimating method comprises a step of respectively measuring the inclination angle of the body, the bending angles respectively of the hip joint and the knee joint of each leg body, and the acceleration of the reference point of the bipedal walking moving body in the absolute coordinate system, for deriving the position of the center of gravity of the bipedal walking moving body relative to the reference point, and so forth, it is not necessary to newly measure them. Further, the rigid body link model may be the same as the rigid body link model used for deriving the position of the center of gravity of the bipedal walking moving body, and so forth.

In the method of estimating a moment of the present invention as described above, by measuring the inclination angle of the body and the bending angles respectively of the hip joints and the knee joints, it is possible to grasp, from those measurement data, inclination angles of the respective rigid-body corresponding portions (these represent a mutual posture relationship of the respective rigid-body corresponding portions), such as the body, the thigh portions, the crus portions, and so forth, of the bipedal walking moving body. Then, based on the weights of the respective rigid-body corresponding portions, the positions of the centers of gravity of the rigid-body corresponding portions in the respective rigid-body corresponding portions (specifically, the positions of the rigid-body corresponding portions in coordinate systems fixed to the respective rigid-body corresponding portions), and the inclination angles of the respective rigid-body corresponding portions, it is possible to derive the positions of the centers of gravity of the respective rigid-body corresponding portions with respect to the reference point. Further, the acceleration of the center of gravity of each rigid-body corresponding portion relative to the reference point is derived as a second-order differentiated value of the position of the center of gravity which is grasped from time series data about the positions of the center of gravity. Therefore, by measuring the acceleration of the reference point in the absolute coordinate system, the acceleration of the center of gravity of each rigid-body corresponding portion of the bipedal walking moving body in the absolute coordinate system can be derived as a composite acceleration of the acceleration of the center of gravity relative to the reference point and the acceleration of the reference point (the acceleration in the absolute coordinate system).

Further, an angular velocity of each rigid-body corresponding portion is derived as a second-order differentiated value of the inclination angle which is grasped from time series data about the inclination angles of each rigid-body corresponding portion.

According to knowledge of the inventors of the present application, the position of a floor reaction force acting point of each leg body in the bipedal walking moving body, for example, the position of a floor reaction force acting point of each leg body relative to the ankle portion of the leg body, has a close correlation with the inclination angle of the thigh portion of each leg body as the rigid-body corresponding portion of the bipedal walking moving body, and the bending angle of the knee joint of each leg body. Therefore, it is possible to derive an estimated position of the floor reaction force acting point in the bipedal walking moving body based on at least one of the inclination angle of the thigh portion of each leg body and the bending angle of the knee joint thereof.

Then, when the accelerations of the centers of gravity of the respective rigid-body corresponding portions of the bipedal walking moving body, the angular velocities of the respective rigid-body corresponding portions, and the estimated position of the floor reaction force acting point are derived as described above, it is possible to estimate moments acting on the knee joint and the hip joint of each leg body based on a known so-called inverse dynamics model, using those data and so forth along with the estimated values of the floor reaction forces derived by the foregoing floor reaction force estimating method. Briefly speaking, the technique based on this inverse dynamics model uses the equation of motion for the translation motion of the center of gravity of each rigid-body corresponding portion of the bipedal walking moving body, and the equation of motion for the rotating motion of the rigid-body corresponding portion (e.g. the rotating motion about the center of gravity of the rigid-body corresponding portion), and derives moments acting on the respective joints of the bipedal walking moving body corresponding to the respective joints of the rigid body link model, in order from the joint closer to the floor reaction force acting point. Although details will be described later, assuming that, for example, each leg body is a linked body having a thigh portion and a crus portion as rigid-body corresponding portions, respectively, a force (joint reaction force) acting on a knee joint of the leg body can be grasped by applying an acceleration of the center of gravity of the crus portion, an estimated value of a floor reaction force acting on the leg body, and a value of the weight of the crus portion, into the equation of motion for the translation motion of the center of gravity of the crus portion of each leg body. Further, a moment on the knee joint of the leg body can be estimated by applying a joint reaction force acting on the knee joint of the leg body, an angular velocity of the crus portion of the leg body, an estimated position of a floor reaction force acting point of the leg body, an estimated value of a floor reaction force on the leg body, data values relating to a position of the center of gravity of the crus portion in the crus portion and a size (length) of the crus portion, a value of a moment of inertia of the crus portion, and a value of an inclination angle of the crus portion, into the equation of motion for the rotating motion of the crus portion.

Further, a joint reaction force acting on a hip joint of the leg body can be grasped by applying an acceleration of the center of gravity of the thigh portion, a joint reaction force acting on the knee joint of the leg body, and a value of the weight of the thigh portion, into the equation of motion for the translation motion of the center of gravity of the thigh portion. Further, a moment on the hip joint of the leg body can be estimated by applying joint reaction forces respectively acting on the knee joint and the hip joint of the leg body, an angular velocity of the thigh portion of the leg body, data values relating to a position of the center of gravity of the thigh portion in the thigh portion and a size (length) of the thigh portion, a value of a moment of inertia of the thigh portion, and a value of an inclination angle of the thigh portion, into the equation of motion for the rotating motion of the thigh portion.

According to the method of estimating a moment of the present invention as described above, by estimating the moments acting on the joints of the leg bodies using the estimated values of the floor reaction forces derived by the foregoing floor reaction force estimating method of the present invention, it is possible to relatively accurately estimate in real time the moments acting on the joints of the leg bodies without attaching the relatively large sensors and so forth to the bipedal walking moving body.

BEST MODE FOR CARRYING OUT THE INVENTION

One embodiment of the present invention will be described with reference to the foregoing FIG. 1 and FIGS. 2 to 10.

The present embodiment is an embodiment wherein a floor reaction force estimating method and a method of estimating a moment of the present invention are applied to a human being as a bipedal walking moving body.

Figure 1:
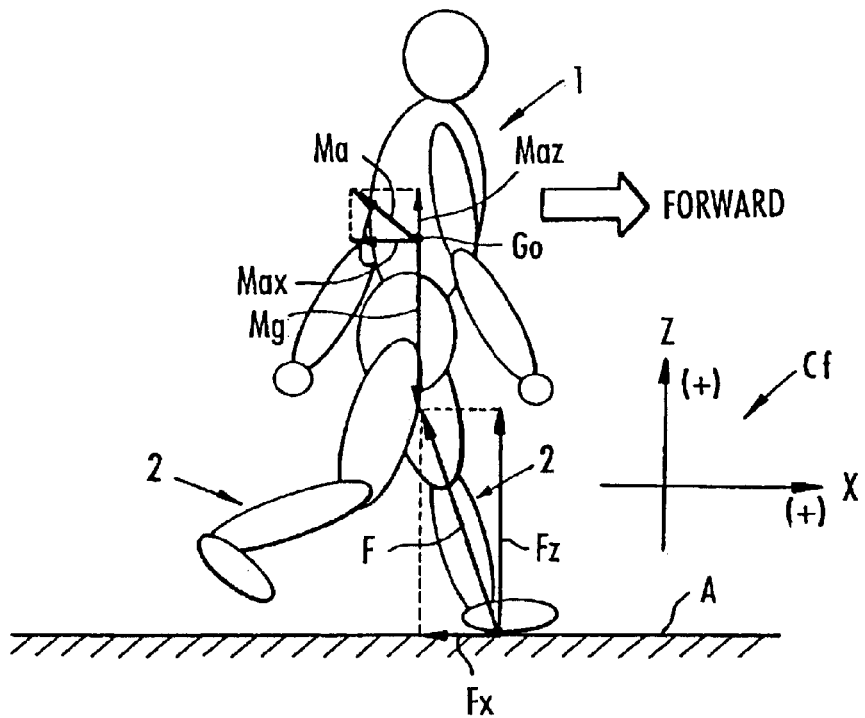
FIG. 1 is a diagram for explaining the basic principle of a floor reaction force estimating method of the present invention.
Figure 1:
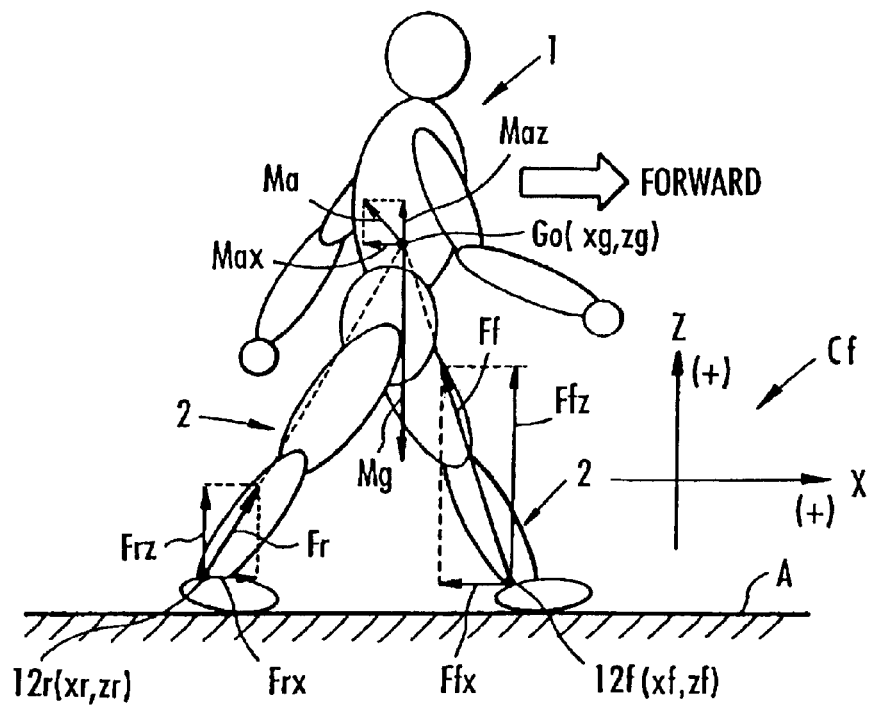
Figure 2:
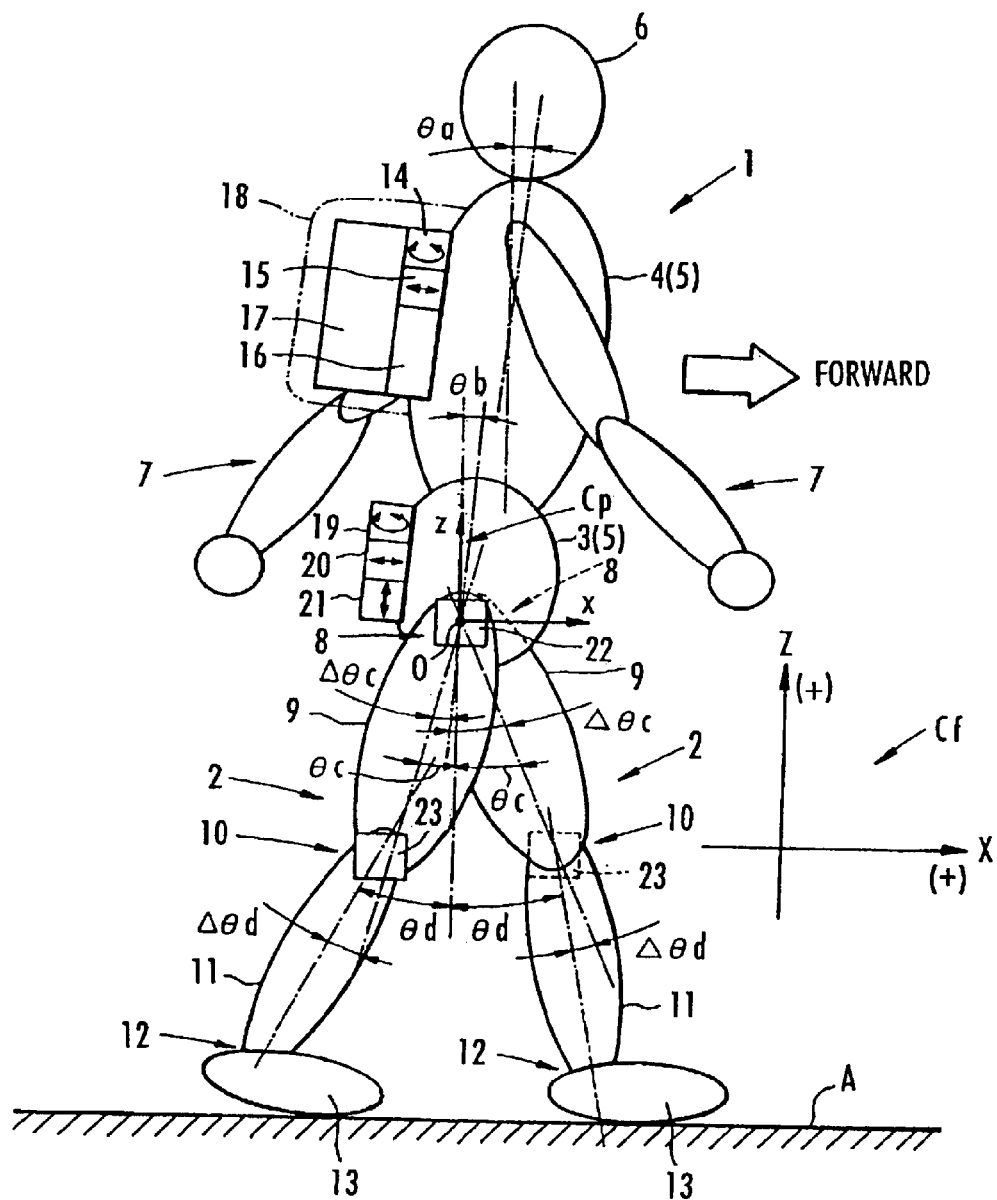
FIG. 2 is a diagram exemplarily showing a human being as a bipedal walking moving body and structures of devices attached to the human being in one embodiment of the present invention.

As exemplarily shown in FIG. 2, a human being 1, when its structure is roughly classified, has a pair of left and right leg bodies 2, 2, a body 5 comprising a waist 3 and a chest 4, a head 6, and a pair of left and right arm bodies 7, 7. The waist 3 is coupled to the respective leg bodies 2, 2 via a pair of left and right hip joints 8, 8 so that the body 5 is supported on both leg bodies 2, 2. Further, the chest 4 of the body 5 is disposed on an upper side of the waist 3 so as to be free inclined toward a forward side of the human being 1 relative to the waist 3. And, the arm bodies 7, 7 extend from both left and right side portions of an upper part of the chest 4, and the head 6 is supported at an upper end portion of the chest 4.

Each of the leg bodies 2, 2 has a thigh portion 9 extending from the hip joint 8, and a crus portion 11 extending from a tip of the thigh portion 9 via a knee joint 10, and a foot portion 13 is coupled to a tip portion of the crus portion 11 via an ankle portion (ankle joint) 12.

In the present embodiment, for estimating a floor reaction force acting on each leg body 2 of the human being 1 having the foregoing structure, and further estimating moments acting on the knee joint 10 and the hip joint 8, the human being 1 is equipped with the following devices.

Specifically, the chest 4 of the body 5 is mounted with a gyro sensor 14 (hereinafter referred to as the chest gyro sensor 14) that produces an output corresponding to an angular velocity following an inclination of the chest 4, an accelerometer 15 (hereinafter referred to as the chest forward/backward accelerometer 15) that produces an output corresponding to an acceleration of the chest 4 in a forward/backward direction, an arithmetic processing unit 16 comprising a CPU, a RAM, a ROM, and so forth, and a battery 17 serving as a power supply for the arithmetic processing unit 16 and so forth. In this case, these chest gyro sensor 14, chest forward/backward accelerometer 15, arithmetic processing unit 16, and battery 17 are, for example, received in a reception member 18 in the form of a shoulder bag that is fixed to the chest 4 using a belt or the like not shown, and unitarily fixed to the chest 4 via the reception member 18.

The acceleration represented by the output of the chest accelerometer 15 is, more specifically, an acceleration in a forward/backward direction in a direction of horizontal section of the chest 4 (a direction perpendicular to a central axis of the chest 4). In the state where the human being 1 is standing erect on a flatland, it is an acceleration in the forward/backward horizontal direction (X-axis direction of the absolute coordinate system in FIG. 2), while, in the state where the waist 3 or the chest 4 is inclined from the vertical direction (Z-axis direction of the absolute coordinate system in FIG. 2), it is an acceleration in a direction inclined relative to the horizontal direction by an inclination angle of the chest 4 relative to the vertical direction.

Further, a gyro sensor 19 (hereinafter referred to as the waist gyro sensor 19) for producing an output corresponding to an angular velocity following an inclination of the waist 3, an accelerometer 20 (hereinafter referred to as the waist forward/backward accelerometer 20) for producing an output corresponding to an acceleration of the waist 3 in a forward/backward direction, and an accelerometer 21 (hereinafter referred to as the waist upward/downward accelerometer 21) for producing an output corresponding to an acceleration of the waist 3 in an upward/downward direction are unitarily mounted/fixed to the waist 3 of the body 5 via fixing means such as a belt not shown.

Here, the waist forward/backward accelerometer 20 is, more specifically, a sensor, like the chest forward/backward accelerometer 15, for detecting an acceleration in a forward/backward direction in a direction of horizontal section of the waist 3 (a direction perpendicular to a central axis of the waist 3). Further, the waist upward/downward accelerometer 21 is, more specifically, a sensor for detecting an acceleration in an upward/downward direction in a direction of the central axis of the waist 3 (this is perpendicular to the acceleration detected by the waist forward/backward accelerometer 20). Incidentally, the waist forward/backward accelerometer 20 and the waist upward/downward accelerometer 21 may be unitarily formed as a two-axis accelerometer.

Further, the hip joint 8 and the knee joint 10 of each leg body 2 are mounted with a hip joint angle sensor 22 and a knee joint angle sensor 23 that produce outputs corresponding to respective bending angles $\Delta\theta c$ and $\Delta\theta d$. With respect to the hip joint angle sensors 22, although only the hip joint angle sensor 22 relating to the hip joint 8 of the leg body 2 on this side (the right side of the human being 1 facing forward) is shown in FIG. 2, the hip joint 8 of the leg body 2 on the other side (the left side of the human being 1 facing forward) is mounted with the hip joint angle sensor 22 concentrically with the hip joint angle sensor 22 on this side.

These angle sensors 22 and 23 are formed by, for example, potentiometers, and attached to each leg body 2 via means such as a band member not shown. Here, the bending angle $\Delta\theta c$ detected by each hip joint angle sensor 22 is, more specifically, a rotation angle of the thigh portion 9 of the leg body 2 about the hip joint 8 (about a central axis of the hip joint 8 in a leftward/rightward direction of the human being 1) relative to the waist 3, using as a criterion the state where a posture relationship between the waist 3 and the thigh portion 9 of the leg body 2 is in a predetermined posture relationship (e.g. a posture relationship in which the central axis of the waist 3 and a central axis of the thigh portion 9 become substantially parallel to each other as in an erect posture state of the human being 1). Likewise, the bending angle $\Delta\theta d$ detected by each knee joint angle sensor 23 is a rotation angle of the crus portion 11 about the knee joint 10 (about a central axis of the knee joint 10 in a leftward/rightward direction of the human being 1) relative to the thigh portion 9, using as a criterion the state where a posture relationship between the thigh portion 9 and the crus portion 11 of the leg body 2 is in a predetermined posture relationship (e.g. a posture relationship in which the central axis of the thigh portion 9 and a central axis of the crus portion 11 become substantially parallel to each other).

Incidentally, the foregoing respective sensors 14, 15, and 19 to 23 are connected to the arithmetic processing unit 16 via signal lines not shown, for inputting outputs thereof into the arithmetic processing unit 16.

Figure 3:
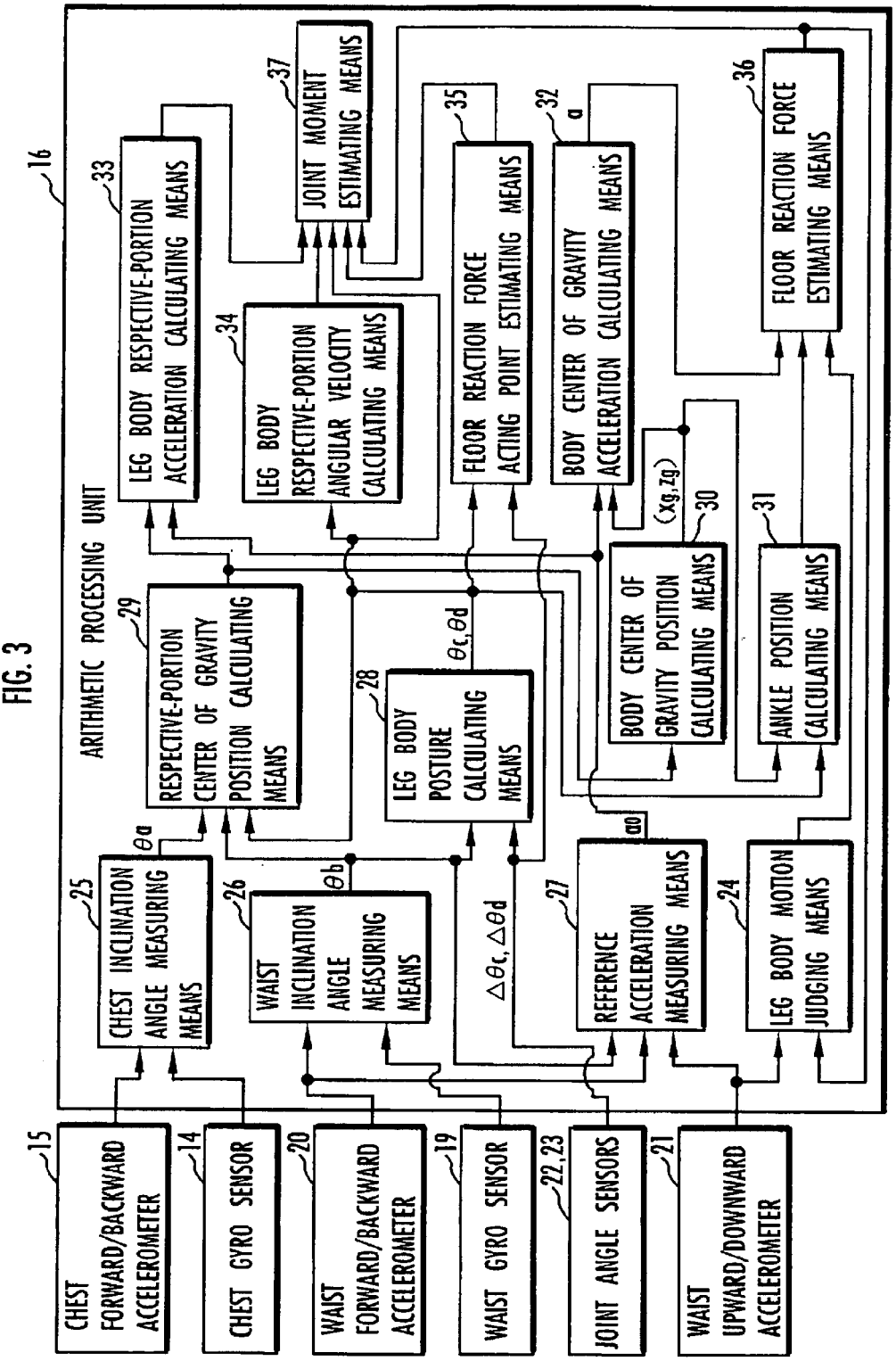
FIG. 3 is a block diagram for explaining functions of an arithmetic processing unit provided in the devices of FIG. 2.

The foregoing arithmetic processing unit 16 is provided with functional means as shown in FIG. 3. Specifically, the arithmetic processing unit 16 is provided with leg body motion judging means 24 for judging whether the motion state of the leg bodies 2, 2 of the human being 1 is the single stance state (state of FIG. 1(a)) or the double stance state (state of FIG. 1(b)), using detection data of the waist upward/downward accelerometer 21 and data about an estimated value of a floor reaction force of each leg body 2 derived by later-described floor reaction force estimating means 36. Further, the arithmetic processing unit 16 is provided with chest inclination angle measuring means 25 for measuring an inclination angle θa of the chest 4 in the absolute coordinate system Cf. (specifically, an inclination angle θa relative to, for example, the vertical direction; see FIG. 2), using detection data of the chest forward/backward accelerometer 15 and the chest gyro sensor 14, and waist inclination angle measuring means 26 for measuring an inclination angle θb of the waist 3 in the absolute coordinate system Cf (specifically, an inclination angle θb relative to, for example, the vertical direction; see FIG. 2), using detection data of the waist forward/backward accelerometer 20 and the waist gyro sensor 19.

Further, the arithmetic processing unit 16 is provided with reference acceleration measuring means 27 for deriving an acceleration (translation acceleration) $a_0 = {}^T(a_0x, a_0z)$, in the absolute coordinate system Cf, of the origin O of a body coordinate system Cp (xz coordinates in FIG. 2) which is set at the waist 3 as a reference point of the human being 1 in the present embodiment as shown in FIG. 2, using detection data of the waist forward/backward accelerometer 20 and the waist upward/downward accelerometer 21 and data about the inclination angle θb of the waist 3 measured by the foregoing waist inclination angle measuring means 26. Here, the body coordinate system Cp is, more specifically, a coordinate system (coordinate system of which directions of three axes are the same as those of the foregoing absolute coordinate system Cf) wherein the origin O is set to, for example, a middle point of a line connecting the respective centers of the left and right hip joints 8, 8 of the human being 1, a z-axis direction is set to the vertical direction, and an x-axis direction is set to the horizontal direction headed forward of the human being 1.

Further, the arithmetic processing unit 16 is provided with leg body posture calculating means 28 for deriving inclination angles θc and θd respectively of the thigh portion 9 and the crus portion 11 of each leg body 2 in the absolute coordinate system Cf (specifically, inclination angles θc and θd relative to, for example, the vertical direction; see FIG. 2), using detection data of the hip joint angle sensor 22 and the knee joint angle sensor 23 of the leg body 2 and data about the inclination angle θb of the waist 3 by the foregoing waist inclination angle measuring means 26.

Further, the arithmetic processing unit 16 is provided with respective-portion center of gravity position calculating means 29 for deriving positions of the centers of gravity of respective rigid-body corresponding portions (specifically, positions of the centers of gravity of respective rigid-body corresponding portions in the foregoing body coordinate system Cp) of the human being 1 corresponding to a later-described rigid body link model, using data about the inclination angle θa of the chest 4, the inclination angle θb of the waist 3, and the inclination angle θc of the thigh portion 9 and the inclination angle θd of the crus portion 11 of each leg body 2 obtained by the foregoing chest inclination angle measuring means 25, waist inclination angle measuring means 26, and leg body posture calculating means 28, body center of gravity position calculating means 30 for deriving a position of the center of gravity of the whole human being 1 in the foregoing body coordinate system Cp, using data about the positions of the centers of gravity of the respective rigid-body corresponding portions, ankle position calculating means 31 for deriving, using data about the position of the center of gravity G0 of the whole human being 1 (see FIG. 1; hereinafter referred to as the body center of gravity G0) and data about the respective inclination angles θc and θd of the thigh portion 9 and the crus portion 11 of each body leg 2 by the foregoing leg body posture calculating means 28, a position of the ankle portion 12 of each leg body 2, as a specific part of each leg 2 in the present embodiment, relative to the body center of gravity G0 (specifically, ΔXf, ΔZf, ΔXr, and ΔZr in the foregoing equations (5)), and body center of gravity acceleration calculating means 32 for deriving an acceleration $a = {}^T(ax, az)$ (see FIG. 1) of the body center of gravity G0 in the absolute coordinate system Cf, using data about the position of the body center of gravity by the foregoing body center of gravity position calculating means 30 and data about the acceleration $a_0$ of the origin O of the body coordinate system Cp by the foregoing reference acceleration measuring means 27.

Further, the arithmetic processing unit 16 is provided with leg body respective-portion acceleration calculating means 33 for deriving accelerations (translation accelerations) of the centers of gravity of the thigh portion 9 and the crus portion 11, respectively, of each leg body 2 in the absolute coordinate system Cf, using data about the positions of the centers of gravity of the respective rigid-body corresponding portions of the human being 1 (specifically, the positions of the centers of gravity of the rigid-body corresponding portions relating to each leg body 2) by the foregoing respective-portion center of gravity position calculating means 29 and data about the acceleration $a_0$ of the origin O of the body coordinate system Cp by the foregoing reference acceleration measuring means 27, leg body respective-portion angular velocity calculating means 34 for deriving angular velocities of the thigh portion 9 and the crus portion 11 of each leg body 2 in the absolute coordinate system Cf, using data about the respective inclination angles θc and θd of the thigh portion 9 and the crus portion 11 of the leg body 2 by the foregoing leg body posture calculating means 28, and floor reaction force acting point estimating means 35 for estimating a position of a floor reaction force acting point of each leg body 2 touching the ground, using data about the inclination angle θc of the thigh portion 9 derived by the foregoing leg body posture calculating means 28 and the bending angle Δθd of the knee joint 10 measured by the foregoing knee joint angle sensor 23.

Further, the arithmetic processing unit 16 is provided with floor reaction force estimating means 36 for deriving an estimated value of a floor reaction force acting on each leg body 2, using data about the acceleration a of the body center of gravity by the foregoing body center of gravity acceleration calculating means 32, data about the position of the ankle portion 12 of each leg body 2 relative to the body center of gravity by the foregoing ankle position calculating means 31, and data about the judgement result on the motion state of the leg bodies 2, 2 by the foregoing leg body motion judging means 24, and joint moment estimating means 37 for estimating moments acting on the knee joint 10 and the hip joint 8, respectively, of each leg body 2, using data about this estimated value of the floor reaction force, data about the accelerations of the centers of gravity of the thigh portion 9 and the crus portion 11 of each leg body 2 by the foregoing leg body respective-portion acceleration calculating means 33, data about the angular velocities of the thigh portion 9 and the crus portion 11 of each leg body 2 by the leg body respective-portion angular velocity calculating means 34, data about the estimated position of the floor reaction force acting point by the floor reaction force acting point estimating means 35, and data about the inclination angles θc and θd of the thigh portion 9 and the crus portion 11, respectively, of each leg body 2 by the foregoing leg body posture calculating means 28.

Now, an operation of this embodiment will be described along with more detailed processing contents of the respective means of the foregoing arithmetic processing unit 16.

In the present embodiment, when the human being 1 turns on a power supply switch, not shown, of the arithmetic processing unit 16 in the state where both leg bodies 2, 2 are on the floor, upon, for example, moving the leg bodies 2, 2, such as walking, the processing by the arithmetic processing unit 16 is executed in sequence per predetermined cycle time as will be described hereinbelow, to thereby successively derive estimated values of floor reaction forces and so forth acting on each leg body 2.

Specifically, at the outset, the arithmetic processing unit 16 executes the processing of the foregoing leg body motion judging means 24. In the processing of the leg body motion judging means 24, detection data about the acceleration of the waist 3 in the upward direction by the foregoing waist upward/downward accelerometer 21 is compared with a prescribed threshold value determined in advance per the foregoing cycle time. Then, when a detected value of the acceleration exceeds the threshold value, it is judged that the double stance state as shown in the foregoing FIG. 1(b) starts, while the single stance state as shown in the foregoing FIG. 1(a) finishes. Specifically, upon transition from the single stance state to the double stance state during walking of the human being 1, landing of the free-leg side leg body 2 on the floor causes the waist 3 near the hip joints 8 to produce a substantially upward and relatively large acceleration (acceleration that can not be produced in the normal single stance state). Therefore, by comparing the detection data about the acceleration of the waist 3 in the upward direction by the waist upward/downward accelerometer 21 with the prescribed threshold value as described above, the foregoing leg body motion judging means 24 judges the start of the double stance state and the finish of the single stance state.

Further, in the processing of the leg body motion judging means 24, of estimated values of floor reaction forces Ff and Fr (see FIG. 1(b)) acting on both leg bodies 2, 2, respectively, which are derived in the double stance state by the floor reaction force estimating means 35 as will be described later, the estimated value of the floor reaction force Fr=$^T$(Frx, Frz) (specifically, an absolute value =√(Frx$^2$+Frz$^2$) of the floor reaction force Fr derived at the previous cycle time of the arithmetic processing unit 16) acting on the leg body 2 on a rear side relative to the advancing direction of the human being is compared with a prescribed threshold value (positive value approximately "0") determined in advance. Then, when the absolute value of the estimated value of the floor reaction force Fr is lowered to the threshold value or less, it is judged that the double stance state finishes and the single stance state starts. In the present embodiment, the initial state of the motion state of the leg bodies 2, 2 is the double stance state, and the leg body motion judging means 24 judges that the motion state of the leg bodies 2, 2 is the double stance state until an estimated value of a floor reaction force acting on either one of the leg bodies 2, 2 is lowered to the foregoing threshold value or less.

In parallel with the processing of the leg body motion judging means 24 as described above, the arithmetic processing unit 16 executes the processing by the foregoing chest inclination angle measuring means 25 and waist inclination angle measuring means 26. In this case, in the processing of the chest inclination angle measuring means 25, an inclination angle θa of the chest 4 in the absolute coordinate system Cf is derived in sequence per the foregoing cycle time according to a known technique using the processing of a so-called Kalman filter, based on detection data about the acceleration of the chest 4 in the forward/backward direction and the angular velocity of the chest 4 which are inputted from the chest forward/backward accelerometer 15 and the chest gyro sensor 14, respectively. Likewise, in the processing of the waist inclination angle measuring means 25, an inclination angle θb of the waist 3 in the absolute coordinate system Cf is derived in sequence using the processing of the Kalman filter, based on detection data about the acceleration of the waist 3 in the forward/backward direction and the angular velocity of the waist 3 which are inputted from the waist forward/backward accelerometer 20 and the waist gyro sensor 19, respectively. Here, in the present embodiment, the inclination angles θa and θb respectively of the chest 4 and the waist 3 in the absolute coordinate system Cf are inclination angles relative to, for example, the vertical direction (direction of gravity).

It is also possible to derive inclination angles of the chest 4 and the waist 3 by, for example, integrating detection data about angular velocities by the gyro sensors 14 and 19. However, like in the present embodiment, the inclination angles θa and θb of the chest 4 and the waist 3 can be accurately measured using the processing of the Kalman filter.

Then, the arithmetic processing unit 16 executes the processing of the foregoing leg body posture calculating means 28 and the processing of the foregoing reference acceleration measuring means 27.

In the processing by the foregoing leg body posture calculating means 28, inclination angles θc and θd (inclination angles relative to the vertical direction; see FIG. 2) of the thigh portion 9 and the crus portion 11 of each leg body 2 in the absolute coordinate system Cf are derived per the foregoing cycle time in the following manner. Specifically, the inclination angle θc of the thigh portion 9 of each leg body 2 is calculated from a current-time value of detection data about the bending angle Δθc of the hip joint 8 by the foregoing hip joint angle sensor 22 attached to the leg body 2 and a current-time value of the inclination angle θb of the waist 3 derived by the foregoing waist inclination angle measuring means 25, using the following equation (6).

$$θc=θb+Δθc \qquad (6)$$

Here, the inclination angle θb of the waist 3 takes a negative value when the waist 3 is inclined relative to the vertical direction such that an upper end portion of the waist 3 is projected forward of the human being 1 as compared with a lower end portion thereof, and the bending angle Δθc of the hip joint 8 takes a positive value when the thigh portion 9 is inclined relative to the central axis of the waist 3 such that a lower end portion of the thigh portion 9 is projected forward of the human being 1.

Further, the inclination angle θd of the crus portion 11 of each leg body 2 is calculated from a current-time value of the inclination angle θc of the thigh portion 9 derived in the foregoing manner and a current-time value of detection data about the bending angle $\Delta\theta d$ of the knee joint 10 by the foregoing knee joint angle sensor 23 attached to the leg body 2, using the following equation (7).

$$\theta d = \theta c - \Delta\theta d \quad (7)$$

Here, the bending angle of the knee joint 10 takes a positive value when the crus portion 11 is inclined relative to the central axis of the thigh portion 9 toward the back side of the thigh portion 9.

Further, in the processing of the foregoing reference acceleration measuring means 27, an acceleration $a_0 = {}^T(a0x, a0z)$ of the origin O of the foregoing body coordinate system Cp in the absolute coordinate system Cf is derived in the following manner. Specifically, given that a current-time value of detection data about the acceleration of the waist 3 in the forward/backward direction by the foregoing waist forward/backward accelerometer 20 is ap, and a current-time value of detection data about the acceleration of the waist 3 in the upward/downward direction by the foregoing waist upward/downward accelerometer 21 is aq, the acceleration $a_0 = {}^T(a_0x, a_0z)$ in the absolute coordinate system Cf is derived from those detection data ap and aq, and a current-time value of the inclination angle $\theta b$ of the waist 3 derived by the foregoing waist inclination angle measuring means 25, using the following equation (8).

$$\begin{aligned} a_0 &= {}^T(a_0x, a_0z) \\ &= {}^T(ap \cdot \cos\theta b - aq \cdot \sin\theta b, ap \cdot \sin\theta b + aq \cdot \cos\theta b - g) \end{aligned} \quad (8)$$

Then, the arithmetic processing unit 16 executes the processing of the foregoing respective-portion center of gravity position calculating means 29, and derives positions (positions relative to the origin of the body coordinate system Cp) of the centers of gravity of respective rigid-body corresponding portions of the human being 1 in the foregoing body coordinate system Cp, using a rigid body link model described hereinbelow.

Figure 4:
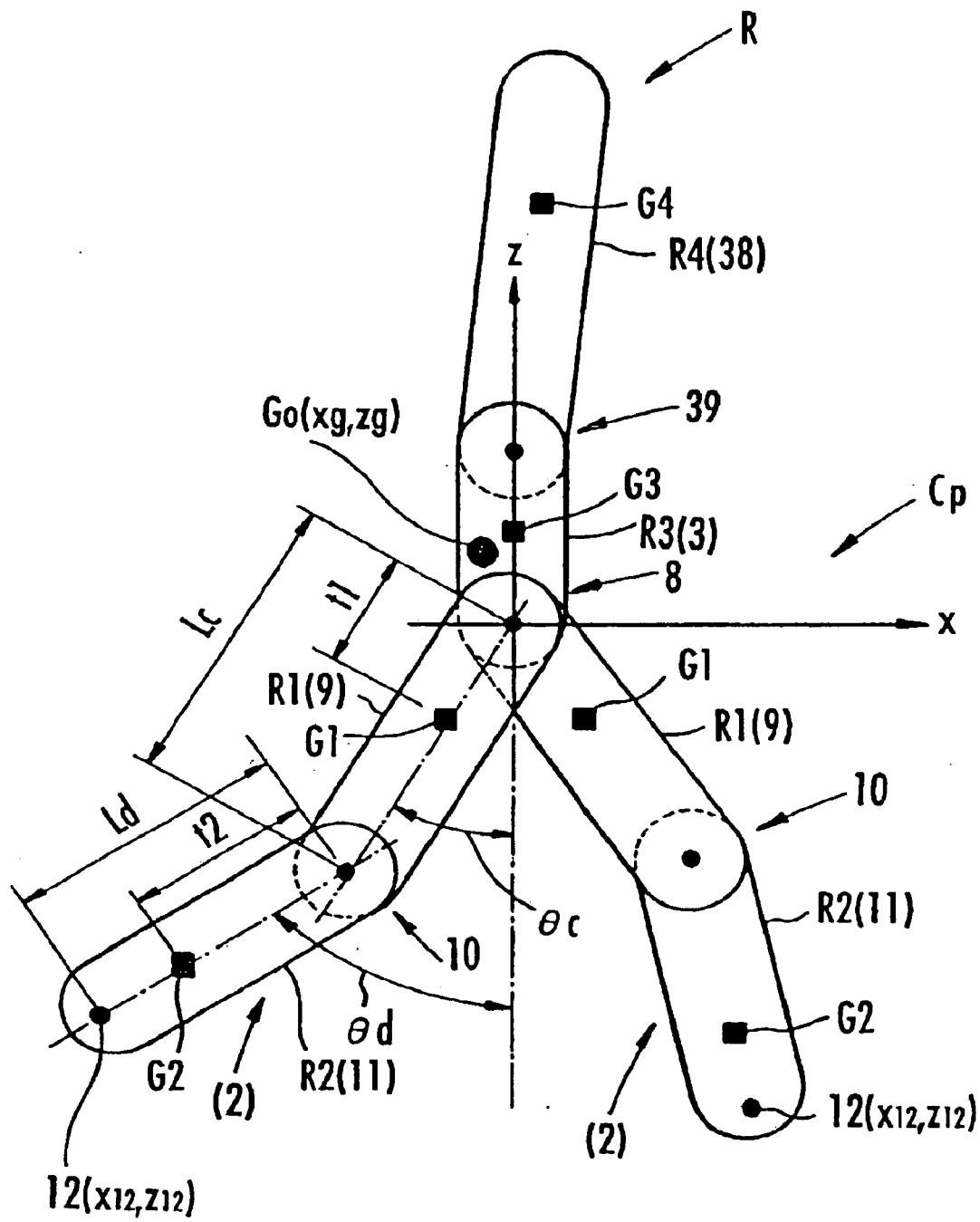
FIG. 4 is a diagram showing a rigid body link model used in the processing of the arithmetic processing unit of FIG. 3.

As shown in FIG. 4, a rigid body link model R used in the present embodiment is a model that expresses the human being 1 by linking together rigid bodies R1, R1 corresponding to the thigh portions 9 of the respective leg bodies 2, 2, rigid bodies R2, R2 corresponding to the crus portions 11, 11, a rigid body R3 corresponding to the waist 3, and a rigid body R4 corresponding to a portion 38 (hereinafter referred to as the upper body portion 38) in a combination of the foregoing chest 4, arm bodies 7, 7, and head 6. In this case, a linkage portion between each rigid body R1 and the rigid body R3, and a linkage portion between each rigid body R1 and the rigid body R2 correspond to the hip joint 8 and the knee joint 10, respectively. Further, a linkage portion between the rigid body R3 and the rigid body R4 is a tilting fulcrum portion 39 for the chest 4 relative to the waist 3.

In the present embodiment, positions of the centers of gravity G1, G2, G3, and G4 of the rigid-body corresponding portions (the thigh portion 9 and the crus portion 11 of each leg body 2, the waist 3, and the upper body portion 38) of the human being 1 corresponding to the respective rigid bodies R1 to R4 of such a rigid body link model R, in the respective rigid-body corresponding portions, are derived in advance and stored in a memory, not shown, of the arithmetic processing unit 16.

Here, the positions of the centers of gravity G1, G2, G3, and G4 of the respective rigid-body corresponding portions stored/retained in the arithmetic processing unit 16 are positions each in a coordinate system that is fixed relative to each rigid-body corresponding portion. In this case, as data representing each of the positions of the centers of gravity G1, G2, G3, and G4 of the respective rigid-body corresponding portions, for example, a distance in a direction of the central axis of the rigid-body corresponding portion from the central point of a joint at one end portion of such a rigid-body corresponding portion is used. Specifically, for example, as shown in FIG. 4, the position of the center of gravity G1 of each thigh portion 9 is given as a position with a distance t1 in the direction of the central axis of the thigh portion 9 from the center of the hip joint 8 of the thigh portion 9, the position of the center of gravity G2 of each crus portion 11 is given as a position with a distance t2 in the direction of the central axis of the crus portion 11 from the center of the knee joint 10 of the crus portion 11, and values of those distances t1 and t2 are derived in advance and stored/retained in the arithmetic processing unit 16. This also applies to the positions of the centers of gravity G3, G4 of the other rigid-body corresponding portions.

Strictly speaking, the position of the center of gravity G4 of the upper body portion 38 is affected by movement of the arm bodies 7, 7 included in the upper body portion 38. However, inasmuch as the arm bodies 7, 7 during walking generally make a symmetrical positional relationship relative to the central axis of the chest 4, the position of the center of gravity G4 of the upper body portion 38 does not change much, and is, for example, substantially equivalent to a position of the center of gravity G4 of the upper body portion 38 in the erect posture state.

Further, in the present embodiment, in addition to the data representing the positions of the centers of gravity G1, G2, G3, and G4 of the respective rigid-body corresponding portions (the thigh portion 9 and the crus portion 11 of each leg body 2, the waist 3, and the upper body portion 38), data about weights of the respective rigid-body corresponding portions, and data about sizes of the respective rigid-body corresponding portions (e.g. data about lengths of the respective rigid-body corresponding portions) are derived in advance and stored/retained in the arithmetic processing unit 16.

The weight of the crus portion 11 is a weight including the foot portion 13. Further, the data stored/retained beforehand in the arithmetic processing unit 16 as described above may be obtained by actual measurement or the like, or may be estimated from a height and weight of the human being 1 based on human average statistical data. In general, the positions of the centers of gravity G1, G2, G3, and G4, the weights, and the sizes of the foregoing respective rigid-body corresponding portions have correlation with a height or weight of a human being and, based on the correlation, it is possible to estimate relatively accurately the positions of the centers of gravity G1, G2, G3, and G4, the weights, and the sizes of the foregoing respective rigid-body corresponding portions from data about the height and weight of the human being.

The foregoing respective-portion center of gravity position calculating means 29 derives positions of the centers of gravity G1, G2, G3, and G4 of the respective rigid-body corresponding portions in the body coordinate system Cp (xz coordinates in FIG. 4) having the origin O fixed to the waist 3, from the data stored/retained beforehand in the arithmetic processing unit 16 as described above, current-time values of the inclination angle $\theta a$ of the chest 4 (=the inclination angle of the upper body portion 38) and the inclination angle $\theta b$ of the waist 3 respectively derived by the foregoing chest inclination angle measuring means 25 and waist inclination angle measuring means 26, and current-time values of the inclination angles θc and θd respectively of the thigh portion 9 and the crus portion 11 of each leg body 2 derived by the foregoing leg body posture calculating means 28.

In this case, since the inclination angles θa to θd of the respective rigid-body corresponding portions (the thigh portion 9 and the crus portion 11 of each leg body 2, the waist 3, and the upper body portion 38) are derived as described above, the positions and postures of the respective rigid-body corresponding portions in the body coordinate system Cp can be derived from data about the inclination angles θa to θd and data about the sizes of the respective rigid-body corresponding portions. Therefore, the positions of the centers of gravity G1, G2, G3, and G4 of the respective rigid-body corresponding portions in the body coordinate system Cp are derived.

Specifically, for example, referring to FIG. 4, with respect to the leg body 2 located on the left side in FIG. 4, since an inclination angle of the thigh portion 9 in the body coordinate system Cp (an inclination angle relative to the z-axis direction) is θc (in this case, θc<0 in FIG. 4), coordinates of the position of the center of gravity G1 of the thigh portion 9 in the body coordinate system Cp become (t1·sin θc, −t1·cos θc). On the other hand, since an inclination angle of the crus portion 11 in the body coordinate system Cp is θd (θd<0 in FIG. 4), given that a length of the thigh portion 9 is Lc, coordinates of the position of the center of gravity G2 of the crus portion 11 in the body coordinate system Cp become (Lc·sin θc+t2·sin θd, −Lc·cos θc−t2·cos θd). The centers of gravity of the thigh portion 9 and the crus portion 11 of the other leg body 2, the waist 3, and the upper body portion 38 can also be derived as described above.

After deriving the positions of the centers of gravity G1, G2, G3, and G4 of the respective rigid-body corresponding portions in the body coordinate system Cp by the respective-portion center of gravity position calculating means 29 as described above, the arithmetic processing unit 16 executes the processing of the foregoing body center of gravity position calculating means 30, and derives a position (xg, zg) of the body center of gravity G0 of the human being 1 in the body coordinate system Cp using data about the positions of the centers of gravity G1, G2, G3, and G4 of the respective rigid-body corresponding portions and data about the weights of the respective rigid-body corresponding portions.

Here, given that the position of the center of gravity G3 of the waist 3 in the body coordinate system Cp and the weight thereof are (x3, z3) and m3, respectively, the position of the center of gravity G4 of the upper body portion 38 and the weight thereof are (x4, z4) and m4, respectively, the position of the center of gravity G1 of the thigh portion 9 of the leg body 2 on the left side of the human being 1 facing forward and the weight thereof are (x1L, z1L) and m1L, respectively, the position of the center of gravity G2 of the crus portion 11 of the same leg body 2 and the weight thereof are (x2L, z2L) and m2L, respectively, the position of the center of gravity G1 of the thigh portion 9 of the leg body 2 on the right side and the weight thereof are (x1R, z1R) and m1R, respectively, the position of the center of gravity G2 of the crus portion 11 of the same leg body 2 and the weight thereof are (x2R, z2R) and m2R, respectively, and the weight of the human being 1 is M (=m1L+m2L+m1R+m2R+m3+m4), the position (xg, zg) of the body center of gravity G0 of the human being 1 in the body coordinate system Cp is derived by the following equations (9).

$$xg = (m1L \cdot x1L + m1R \cdot x1R + m2L \cdot x2L + m2R \cdot x2R + m3 \cdot x3 + m4 \cdot x4)/M \quad (9)$$

$$zg = (m1L \cdot z1L + m1R \cdot z1R + m2L \cdot z2L + m2R \cdot z2R + m3 \cdot z3 + m4 \cdot z4)/M$$

After executing the processing of the body center of gravity position calculating means 30 as described above, the arithmetic processing unit 16 further executes the processing of the foregoing body center of gravity acceleration calculating means 32 and the processing of the foregoing ankle position calculating means 31.

In this case, in the processing of the body center of gravity acceleration calculating means 32, at the outset, using time series data about the positions (xg, zg) of the body center of gravity G0 in the body coordinate system Cp derived by the body center of gravity position calculating means 30 per the foregoing cycle time, a second-order differentiated value of the position (xg, zg) of the body center of gravity G0 in the body coordinate system Cp, that is, an acceleration $^T(d^2xg/dt^2, d^2zg/dt^2)$ of the body center of gravity G0 relative to the origin O of the body coordinate system Cp, is derived. Then, by deriving the vector sum of the acceleration $^T(d^2xg/dt^2, d^2zg/dt^2)$ and the acceleration $a_0 = {}^T(a_0x, a_0z)$, derived by the foregoing reference acceleration measuring means 27, of the origin O of the body coordinate system Cp in the absolute coordinate system Cf, an acceleration $a = {}^T(ax, az)$ of the body center of gravity G0 in the absolute coordinate system Cf is derived.

Further, in the processing of the foregoing ankle position calculating means 31, at the outset, from current-time values of data about the inclination angles θc and θd respectively of the thigh portion 9 and the crus portion 11 of each leg body 2 derived by the foregoing leg body posture calculating means 28, a current-time value of data about the inclination angle θb of the waist 3 derived by the foregoing waist inclination angle measuring means 26, and data about the sizes (lengths) of the thigh portion 9 and the crus portion 11, a position of the ankle portion 12 of each leg body 2 in the foregoing body coordinate system Cp is derived by the processing like the processing of the foregoing respective-portion center of gravity position calculating means 29. Specifically, referring to FIG. 4, with respect to the leg body 2 located on the left side in FIG. 4, given that a length of the crus portion 11 (a length from the center of the knee joint 10 to the ankle portion 12) is Ld, coordinates (x12, z12) of the position of the ankle portion 12 in the body coordinate system Cp become (Lc·sin θc+Ld·sin θd, −Lc·cos θc−Ld·cos θd) (wherein θc<0 and θd<0 in FIG. 4). This also applies to the other leg body 2.

Then, from current-time values of data about the position (x12, z12) of the ankle portion 12 in the body coordinate system Cp and the position (xg, zg) of the body center of gravity G0 in the body coordinate system Cp derived by the foregoing body center of gravity position calculating means 30, a position vector $^T(x12-xg, z12-zg)$ of the ankle portion 12 of each leg body 2 relative to the body center of gravity G0, that is, ΔXf, ΔZf, ΔXr, and ΔZr in the foregoing equations (5), are derived.

Then, the arithmetic processing means 16 executes the processing of the foregoing floor reaction force estimating means 36 in the following manner. Specifically, in this processing, when the motion state of the leg bodies 2, 2 determined by the foregoing leg body motion judging means 24 at the current cycle time is the single stance state, an estimated value of a floor reaction force $F = {}^T(Fx, Fz)$ acting on the leg body 2 touching the ground is derived from values of the weight M and the acceleration of gravity g of the human being 1 (these are stored beforehand in the arithmetic processing unit 16) and a current-time value of the acceleration $a = {}^T(ax, az)$ of the body center of gravity G0 in the absolute coordinate system Cf derived by the foregoing body center of gravity acceleration calculating means 32, using the foregoing equation (2). In this case, a floor reaction force acting on the ground non-touching side leg body 2 (the free-leg side leg body 2) is ${}^T(0, 0)$.

On the other hand, when the motion state of the leg bodies 2, 2 determined by the leg body motion judging means 24 at the current cycle time is the double stance state, estimated values of floor reaction forces $Ff = {}^T(Ffx, Ffz)$ and $Fr = {}^T(Frx, Frz)$ on the respective leg bodies 2, 2 are derived from the weight M and the acceleration of gravity g of the human being 1, a current-time value of the acceleration $a = {}^T(ax, az)$ of the body center of gravity G0 in the absolute coordinate system Cf derived by the foregoing body center of gravity acceleration calculating means 32, and current-time value data about the position of the ankle portion 12 of each leg body 2 relative to the body center of gravity G0 (current-time values of data about $\Delta Xf$, $\Delta Zf$, $\Delta Xr$, and $\Delta Zr$ in the equations (5)) derived by the foregoing ankle position calculating means 31, using the foregoing equations (5).

On the other hand, in parallel to the processing of the body center of gravity position calculating means 30, the body center of gravity acceleration calculating means 32, the ankle position calculating means 31, and the floor reaction force estimating means 36 as described above, the arithmetic processing unit 16 executes the processing of the foregoing leg body respective-portion acceleration calculating means 33, leg body respective-portion angular velocity calculating means 34, and floor reaction force acting point estimating means 35.

In this case, in the processing of the foregoing leg body respective-portion acceleration calculating means 33, at the outset, like in the foregoing body center of gravity acceleration calculating means 32, using time series data about the positions of the centers of gravity G1 and G2 respectively of the thigh portion 9 and the crus portion 11 being the rigid-body corresponding portions of each leg body 2 in the body coordinate system Cp, which are derived by the foregoing respective-portion center of gravity position calculating means 29 per the foregoing cycle time, second-order differentiated values of the positions of the centers of gravity G1 and G2 respectively of the thigh portion 9 and the crus portion 11 in the body coordinate system Cp, that is, accelerations (accelerations relative to the origin O of the body coordinate system Cp) of the respective centers of gravity G1 and G2 of the thigh portion 9 and the crus portion 11 in the body coordinate system Cp, are derived. Then, by deriving the vector sum of these respective accelerations and the acceleration $a_0 = {}^T(a_0x, a_0z)$ of the waist 3 in the absolute coordinate system Cf by the foregoing reference acceleration measuring means 27, accelerations (more specifically, coordinate components of the accelerations in the absolute coordinate system Cf) respectively of the thigh portion 9 and the crus portion 11 in the absolute coordinate system Cf are derived.

Further, in the processing of the foregoing leg body respective-portion angular velocity calculating means 34, using time series data about the inclination angles θc and θd respectively of the thigh portion 9 and the crus portion 11 of each leg body 2 derived by the foregoing leg body posture calculating means 28 per the foregoing cycle time, second-order differentiated values of the respective inclination angles θc and θd of the thigh portion 9 and the crus portion 11, that is, angular velocities respectively of the thigh portion 9 and the crus portion 11, are derived.

Figure 5:
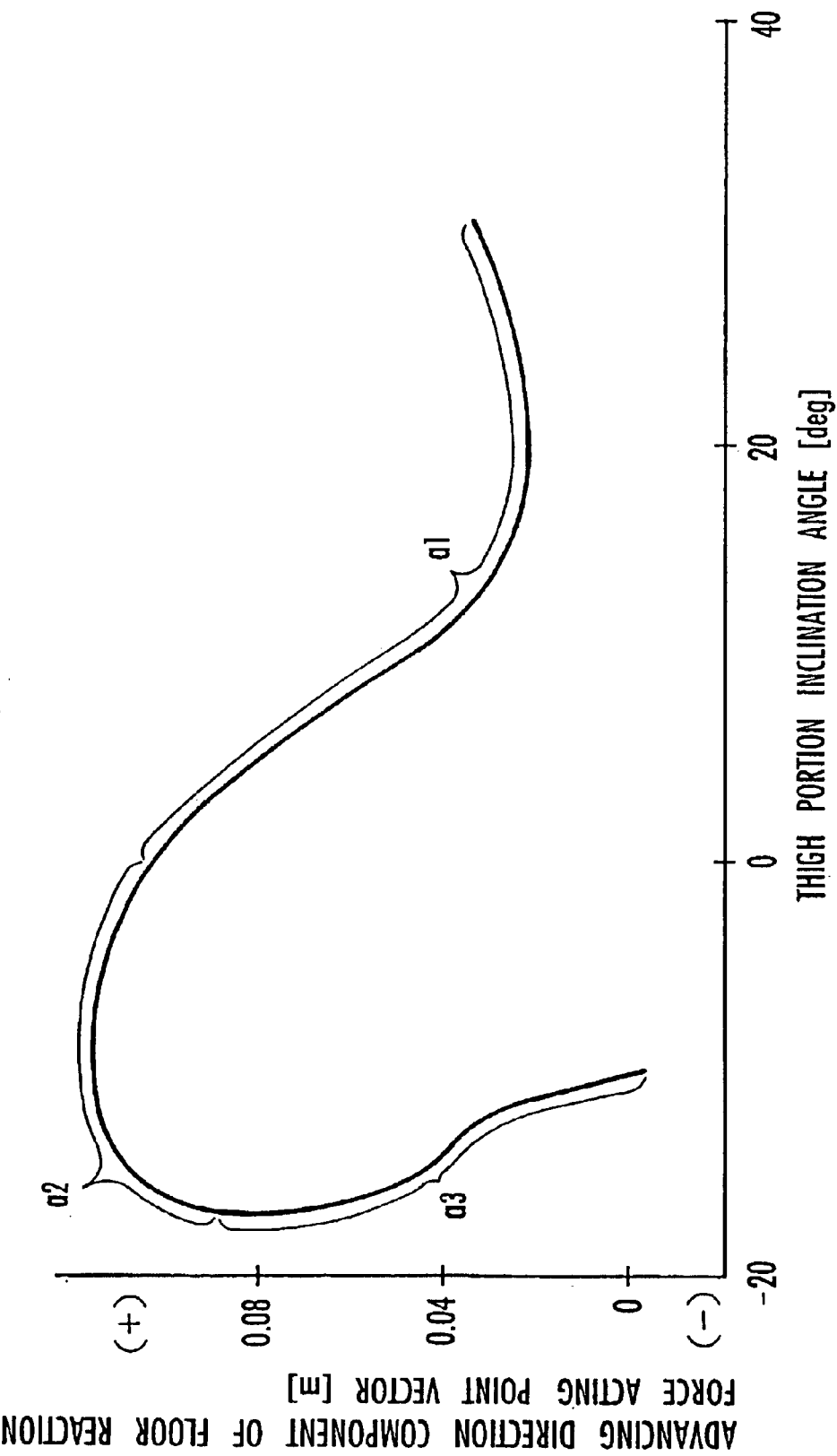
FIG. 5 is a diagram showing a correlation between advancing direction components of a floor reaction force acting point vector and an inclination angle of a thigh portion during normal walking.
Figure 6:
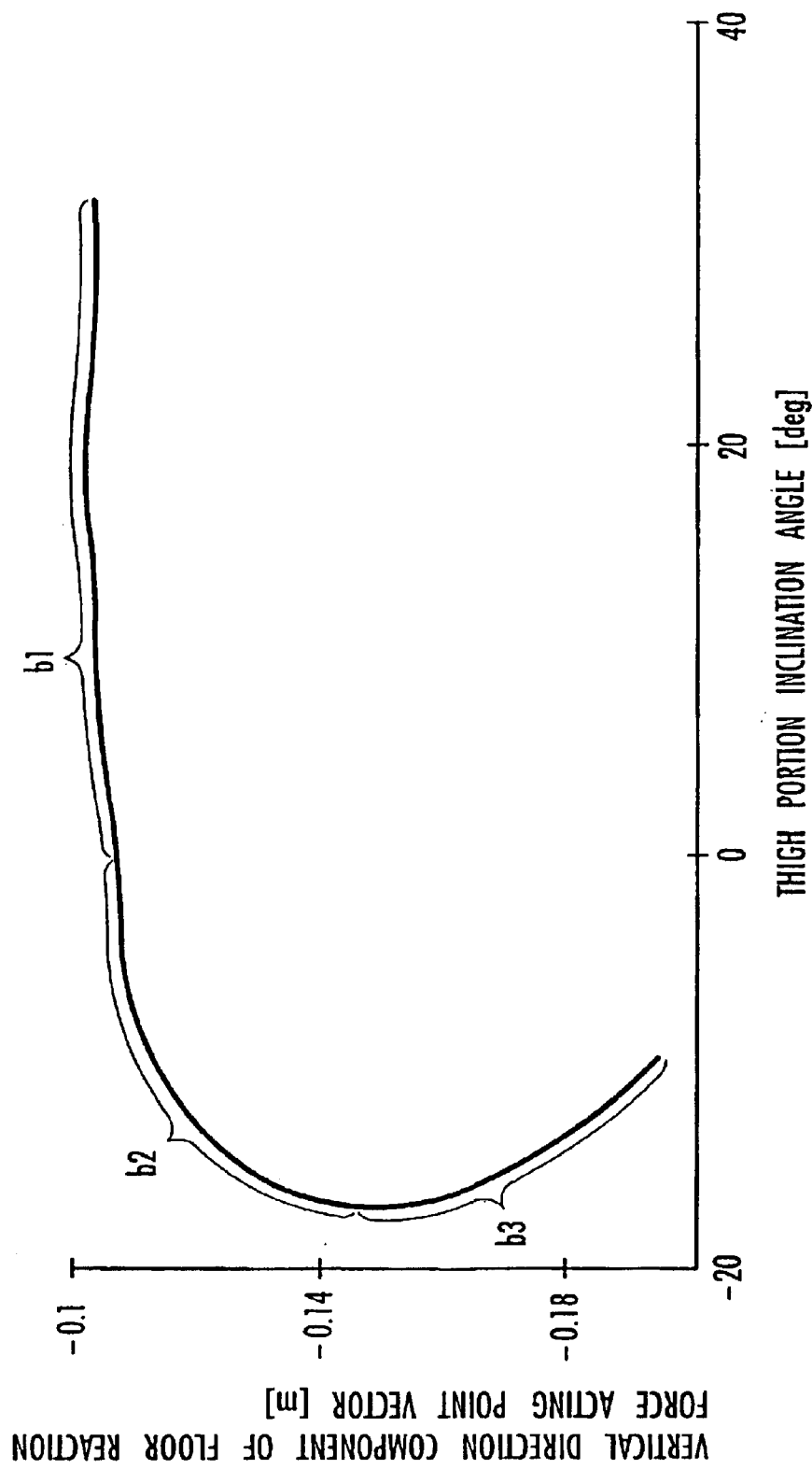
FIG. 6 is a diagram showing a correlation between vertical direction components of a floor reaction force acting point vector and an inclination angle of a thigh portion during normal walking.

Further, in the processing of the floor reaction force acting point estimating means 35, with respect to the leg body 2 touching the ground, a vector (position vector of a floor reaction force acting point relative to the ankle portion 12; hereinafter referred to as the floor reaction force acting point vector) from the ankle portion 12 of the leg body 2 to a floor reaction force acting point of the foot portion 13 of the leg body 2 (a point upon which the total floor reaction force acting on a ground touching portion of the foot portion 13 is considered to be concentrated) is derived as data representing a position of the floor reaction force acting point, from, for example, a current-time value of the inclination angle θc of the thigh portion 9 derived by the foregoing leg body posture calculating means 28, based on predetermined correlations as shown in FIGS. 5 and 6.

Specifically, according to knowledge of the inventors of the present application, the inclination angle θc of the thigh portion 9 or the bending angle $\Delta\theta d$ of the knee joint 10 of the leg body 2 touching the ground has relatively significant correlation with the floor reaction force acting point. The foregoing floor reaction force acting point vector, specifically, components of the floor reaction force acting point vector in the advancing direction (X-axis direction) of the human being 1, and components of the floor reaction force acting point vector in the vertical direction (Z-axis vector), respectively change with respect to, for example, the inclination angle θc of the thigh portion 9 as shown in FIGS. 5 and 6. Here, the negative inclination angle θc of the thigh portion 9 is an angle when the thigh portion 9 is inclined relative to the central axis of the waist 3 so that the leg body 2 extends to the back side of the human being 1 (e.g. the leg body 2 on the right side of the human being 1 facing forward in FIG. 2), while the positive inclination angle θc is an angle when the thigh portion 9 is inclined relative to the central axis of the waist 3 so that the leg body 2 exists on the front side of the human being 1 (e.g. the leg body 2 on the left side of the human being 1 facing forward in FIG. 2).

Therefore, in the present embodiment, approximate expressions using the inclination angle θc of the thigh portion 9 as a parameter, which represent the correlations of FIGS. 5 and 6, are prepared and stored/retained in advance in the arithmetic processing unit 16. Then, in the processing of the foregoing floor reaction force acting point estimating means 35, a current-time value of the inclination angle θc of the thigh portion 9 derived by the foregoing leg body posture calculating means 28 is put in the foregoing approximate expressions to thereby derive the foregoing floor reaction force acting point vector (specifically, components of the floor reaction force acting point vector in the X-axis direction and Z-axis direction).

Here, in the correlations as shown in FIGS. 5 and 6 wherein the inclination angle θc of the thigh portion 9 has a minimal value, even when the inclination angle θc of the thigh portion 9 is the same, a value of the floor reaction force acting point vector differs between a decreasing stage of the inclination angle θc and an increasing stage thereof. Therefore, in the present embodiment, upon preparing the foregoing approximate expression, a transition of the foregoing correlation from a landing of the heel of the foot portion 13 on the floor to a takeoff of the tiptoe from the floor is classified into a first phase (a phase of a1 in FIG. 5; a phase of b1 in FIG. 6) wherein the inclination angle θc of the thigh portion 9 is positive, a second phase (a phase of a2 in FIG. 5; a phase of b2 in FIG. 6) wherein the inclination angle θc of the thigh portion 9 is negative, and a changing speed of the inclination angle θc of the thigh portion 9, i.e. an inclination angular velocity of the thigh portion 9, is negative, and a third phase (a phase of a3 in FIG. 5; a phase of b3 in FIG. 6) wherein the inclination angle θc of the thigh portion 9 is negative, and an inclination angular velocity of the thigh portion 9 is positive, and the phases are approximated by the same function or different functions with respect to X-axis direction components and Z-axis direction components of the floor reaction force acting point vector, respectively. An approximate expression of a phase in a combination of the first and second phases a1 and a2 in the correlation of FIG. 5 is, given that the X-axis direction components of the floor reaction force acting point vector are px, expressed by, for example, a sixth-order polynomial function in the form of $$px = x_1 \cdot \theta c^6 + x_2 \cdot \theta c^5 + x_3 \cdot \theta c^4 + x_4 \cdot \theta c^3 + x_5 \cdot \theta c^2 + x_6 \cdot \theta c + x_7$$

($x_1$ to $x_7$ are constant values).
Further, an approximate expression of the third phase a3 in the correlation of FIG. 5 is expressed by, for example, a fourth-order polynomial function in the form of $$px = x_8 \cdot \theta c^4 + x_9 \cdot \theta c^3 + x_{10} \cdot \theta c^2 + x_{11} \cdot \theta c + x_{12}$$

($x_8$ to $x_{12}$ are constant values).
Further, an approximate expression of a phase in a combination of the first and second phases b1 and b2 in the correlation of FIG. 6 is, given that the Z-axis direction components of the floor reaction force acting point vector are pz, expressed by, for example, a sixth-order polynomial function in the form of $$pz = z_1 \cdot \theta c^6 + z_2 \cdot \theta c^5 + z_3 \cdot \theta c^4 + z_4 \cdot \theta c^3 + z_5 \cdot \theta c^2 + z_6 \cdot \theta c + z_7$$

($z_1$ to $z_7$ are constant values)
Further, an approximate expression of the third phase b3 in the correlation of FIG. 6 is expressed by, for example, a third-order polynomial function in the form of $$pz = z_8 \cdot \theta c^3 + z_9 \cdot \theta c^2 + z_{10} \cdot \theta c + z_{11}$$

($x_8$ to $x_{11}$ are constant values)
Then, upon deriving the floor reaction force acting point vector, it is judged whether the inclination angle θc of the thigh portion 9 is positive or negative, and further judged whether the inclination angular velocity of the thigh portion 9 calculated by first-order differentiation of time series data about the inclination angles θc of the thigh portion 9 is positive or negative. Further, from judged positive or negative of the inclination angle θc and judged positive or negative of the inclination angular velocity, it is judged which of the phases is manifested currently and, by putting a current-time value of the inclination angle θc of the thigh portion 9 into the approximate expression of the judged phase, the floor reaction force acting point vector is calculated. Thereby, the value of the floor reaction force acting point vector in the decreasing stage of the inclination angle θc of the thigh portion 9, and the value of the floor reaction force acting point vector in the increasing stage thereof can be discriminatingly calculated.

In the present embodiment, the correlation between the inclination angle θc of the thigh portion 9 of the leg body and the floor reaction force acting point vector is approximated by the polynomials to thereby derive the floor reaction force acting point vector. However, it is also possible to store/retain the correlations shown in FIGS. 5 and 6 in the form of a data table and, using the data table, derive the floor reaction force acting point vector from the inclination angle θc of the thigh portion 9.

Further, the position of the floor reaction force acting point also has correlation with the bending angle of the knee joint 10 of the leg body 2 touching the ground. Therefore, the position of the floor reaction force acting point may be estimated from the bending angle Δθd of the knee joint 10 measured by the knee joint angle sensor 23, instead of the inclination angle θc of the thigh portion 9. Alternatively, using both the inclination angle θc of the thigh portion 9 and the bending angle Δθd of the knee joint 10, the position of the floor reaction force acting point may be estimated by the use of a map or the like.

Figure 7:
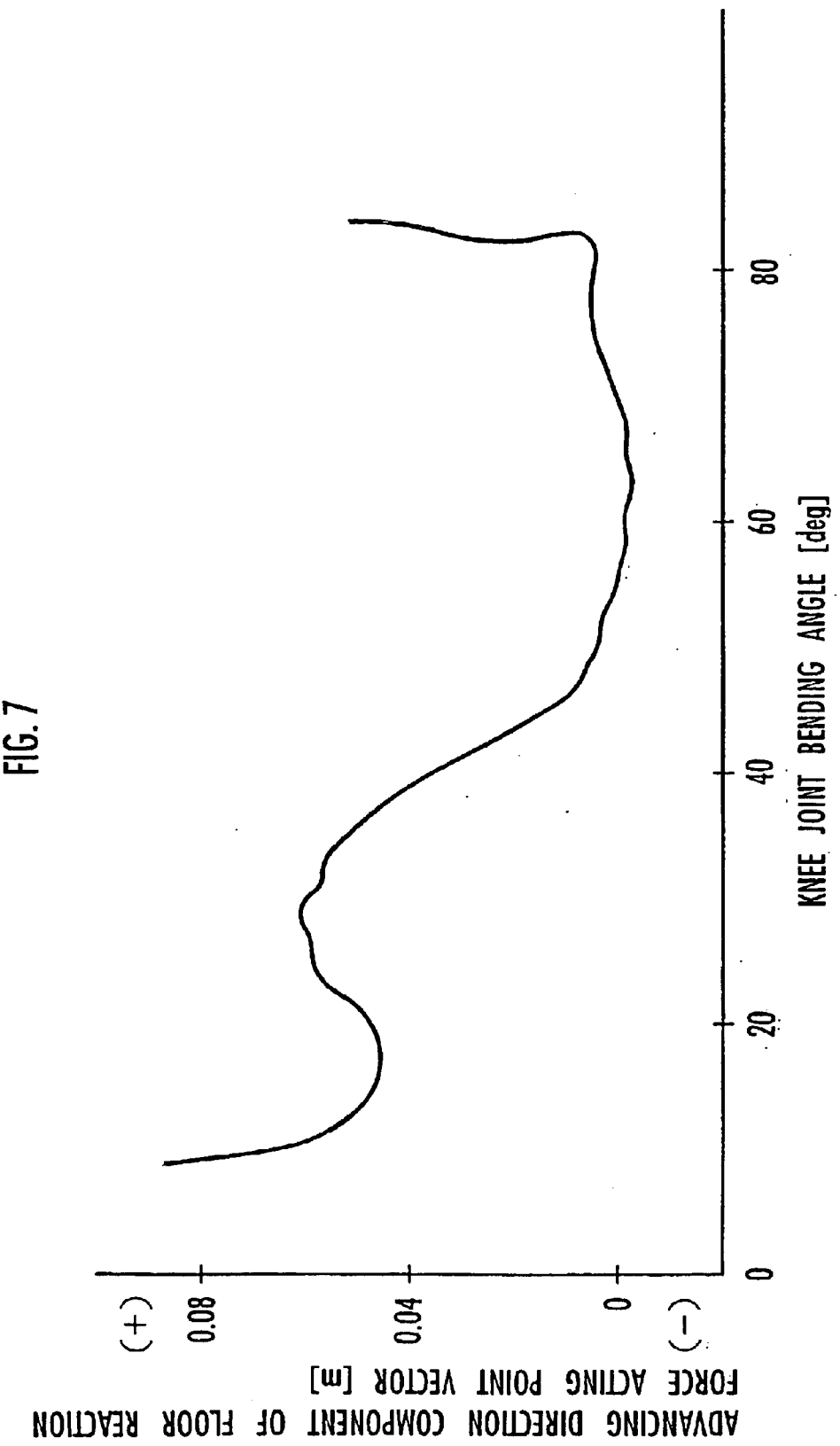
FIG. 7 is a diagram showing a correlation between advancing direction components of a floor reaction force acting point vector and a bending angle of a knee joint upon sitting in a chair.
Figure 8:
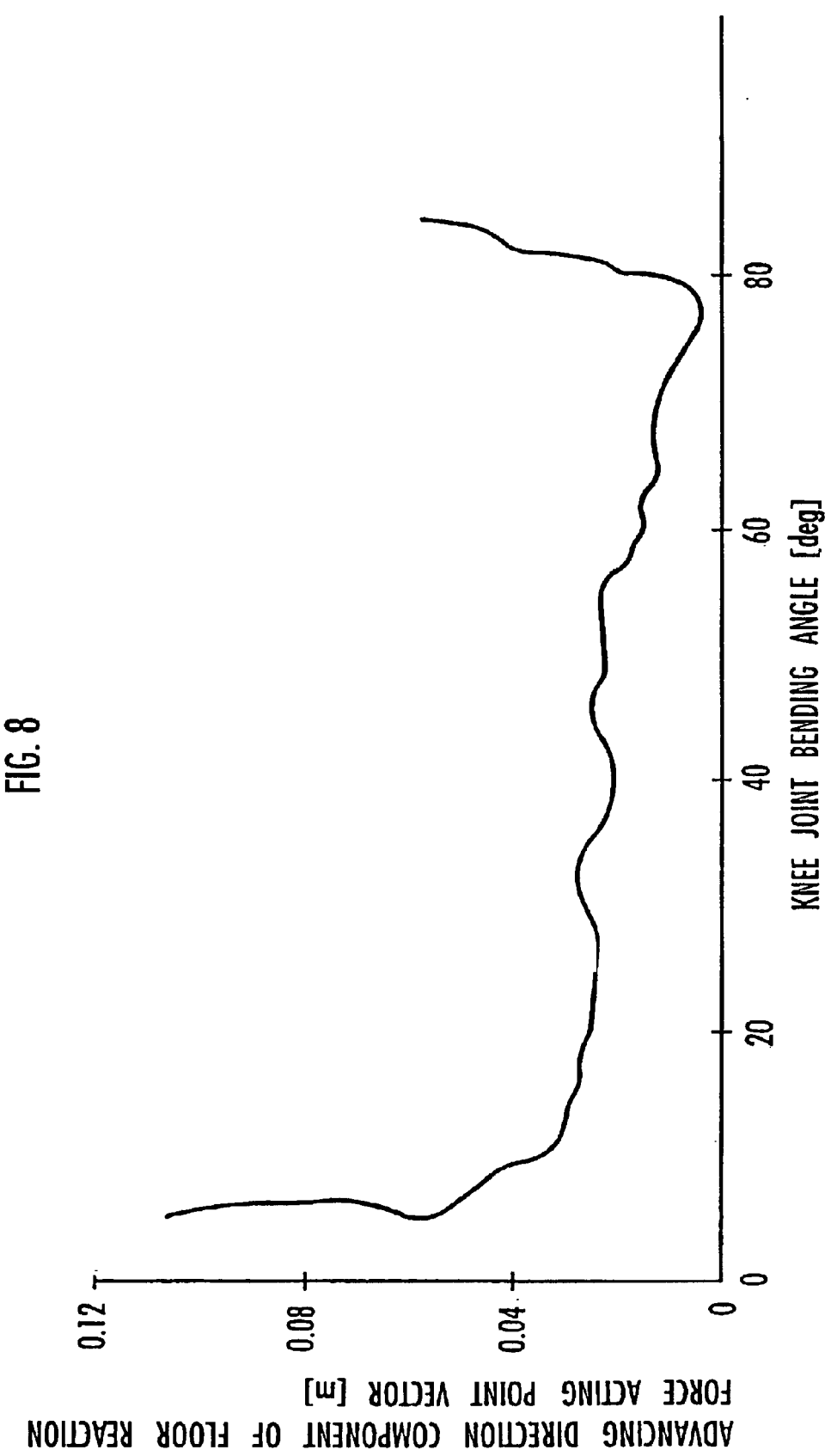
FIG. 8 is a diagram showing a correlation between advancing direction components of a floor reaction force acting point vector and a bending angle of a knee joint upon standing up from a chair.
Figure 9:
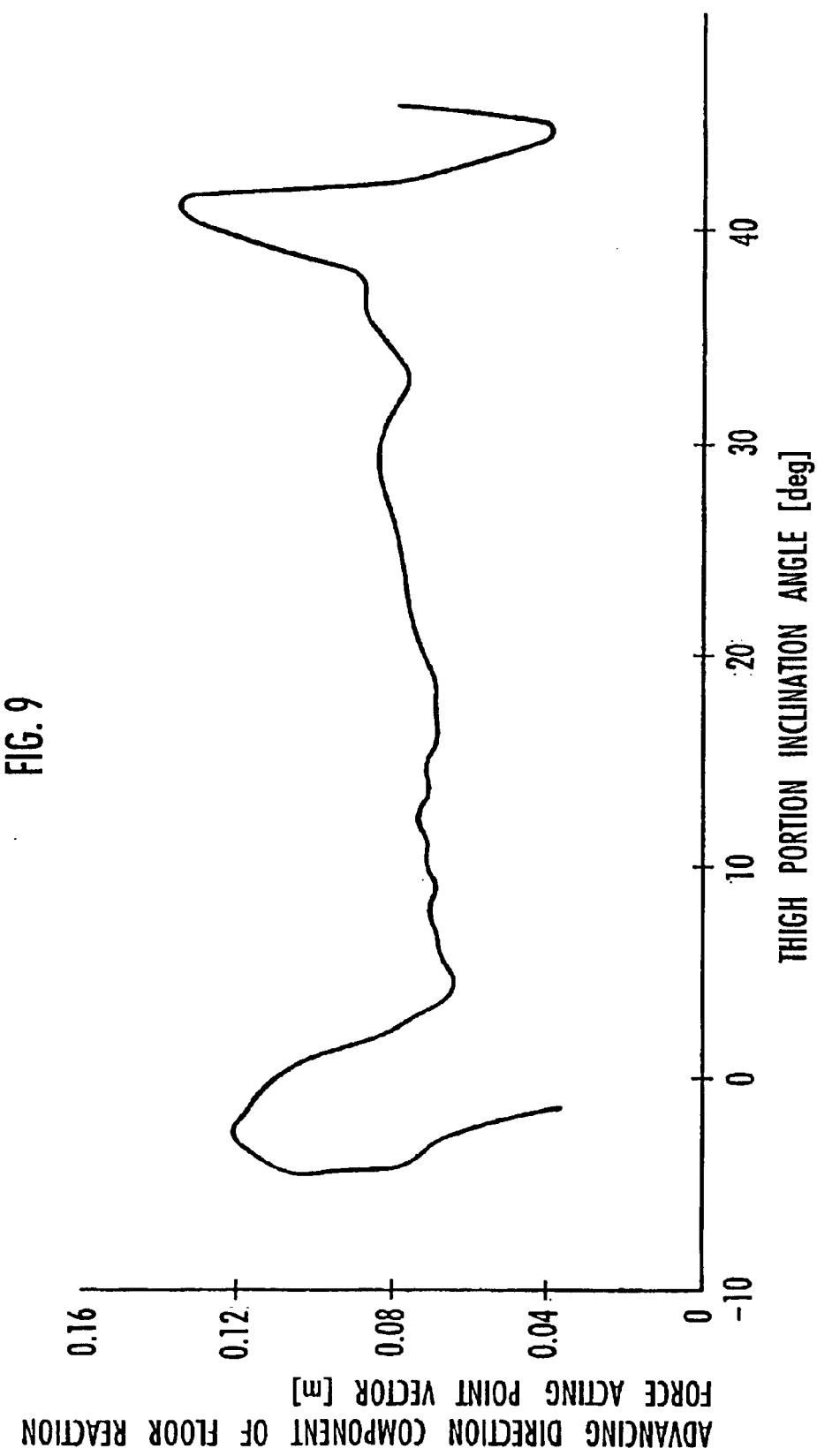
FIG. 9 is a diagram showing a correlation between advancing direction components of a floor reaction force acting point vector and an inclination angle of a thigh portion upon going upstairs.
Figure 10:
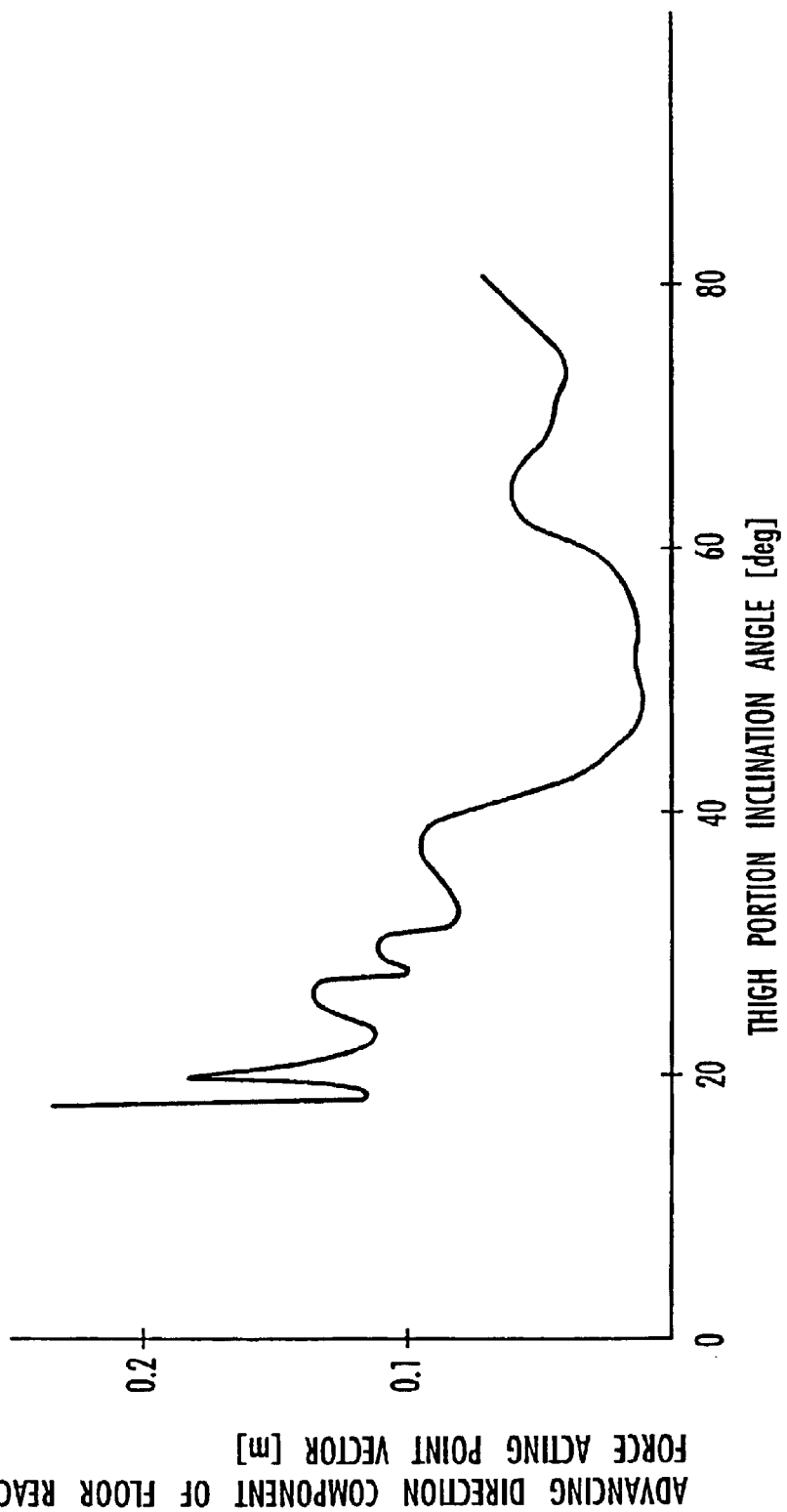
FIG. 10 is a diagram showing a correlation between advancing direction components of a floor reaction force acting point vector and an inclination angle of a thigh portion upon going downstairs.

Further, when the human being 1 sits in a chair or stands up from the state of sitting in the chair, a correlation shown in FIG. 7 (upon sitting in the chair) or FIG. 8 (upon standing up from the chair) is established between the position of the floor reaction force acting point and the bending angle Δθd of the knee joint 10 and, when going upstairs or downstairs, FIG. 9 (upon going upstairs) or FIG. 10 (upon going downstairs) is established between the position of the floor reaction force acting point and the inclination angle θc of the thigh portion 9. Therefore, upon sitting in the chair or standing up, the position of the floor reaction force acting point can be estimated from the bending angle Δθd of the knee joint 10 based on the correlation of FIG. 7 or FIG. 8, while, upon going upstairs or downstairs, the position of the floor reaction force acting point can be estimated from the inclination angle θc of the thigh portion 9 based on the correlation of FIG. 9 or FIG. 10.

After estimating the position of the floor reaction force acting point as described above, then, the arithmetic processing unit 16 executes the processing of the foregoing joint moment estimating means 37, and derives moments acting on the knee joint 10 and the hip joint 8 of each leg body 2. This processing is carried out based on a so-called inverse dynamics model using current-time values of the data respectively derived by the foregoing floor reaction force estimating means 36, leg body respective-portion acceleration calculating means 33, leg body respective-portion angular velocity calculating means 34, floor reaction force acting point estimating means 35, and leg body posture calculating means 28. This inverse dynamics model uses an equation of motion for translation motion of each rigid-body corresponding portion of the human being 1 and an equation of motion for rotating motion thereof so as to derive moments acting on joints in order from the joint closer to the floor reaction force acting point. In the present embodiment, the moments acting on the knee joint 10 and the hip joint 8 of each leg body 2 are derived in order.

Figure 11:
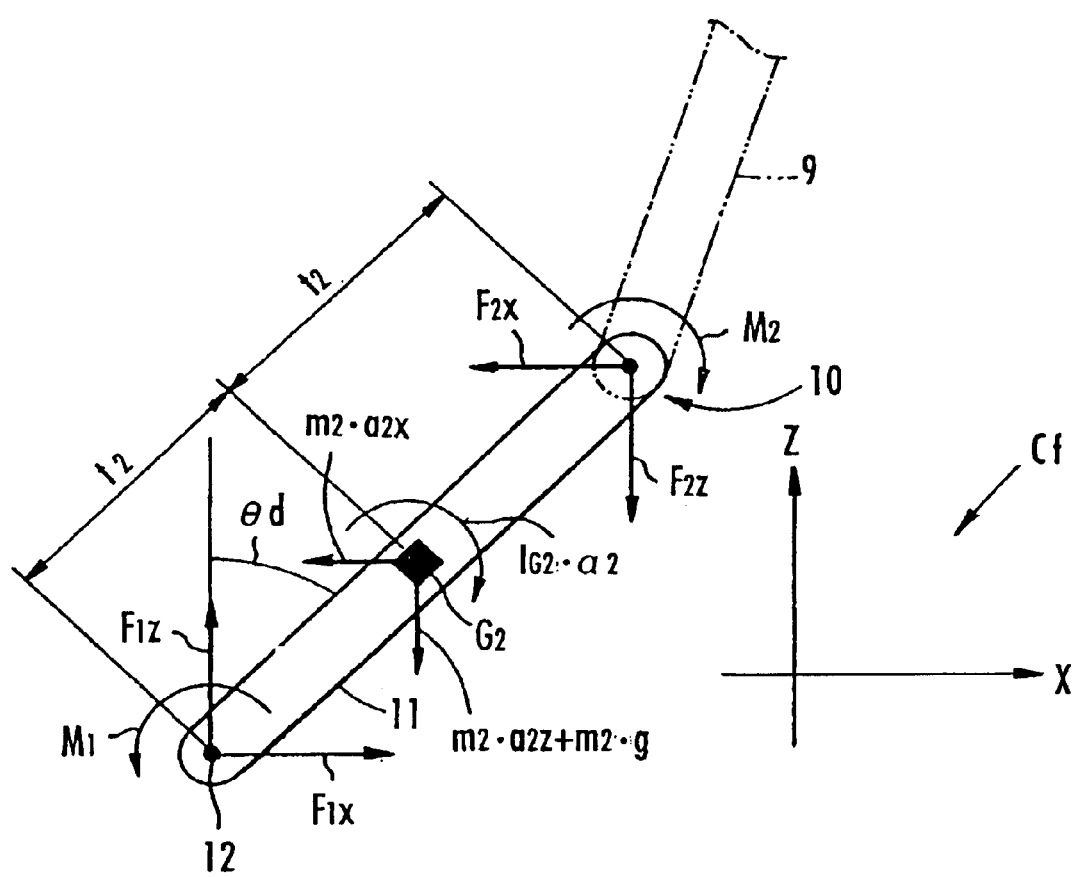
FIG. 11 is a diagram for explaining the processing in joint moment estimating means of the arithmetic processing unit of FIG. 3.

More specifically, referring to FIG. 11, at the outset, with respect to the crus portion 11 of each leg body 2, a force (joint reaction force) acting on the ankle portion 12 at a tip portion of the crus portion 11, a force (joint reaction force) acting on the portion of the knee joint 10 of the crus portion 11, and a translation acceleration of the center of gravity G2 of the crus portion 11 are respectively given as $^T(F_1x, F_1z)$, $^T(F_2x, F_2z)$, and $^T(a_2x, a_2z)$ according to the component notation in the absolute coordinate system Cf, and the weight of the crus portion 11 is given as $m_2$. In this case, an equation of motion for the translation motion of the center of gravity G2 of the crus portion 11 becomes the following equation (10).

$$^T(m_2 \cdot a_2x, m_2 \cdot a_2z) = {}^T(F_1x - F_2x, F_1z - F_2z - m_2 \cdot g)$$

therefore, $$^T(F_2x, F_2z) = {}^T(F_1x - m_2 \cdot a_2x, F_1z - m_2 \cdot a_2z - m_2 \cdot g) \quad (10)$$

Here, the acceleration $^T(a_2x, a_2z)$ of the center of gravity G2 of the crus portion 11 is derived by the foregoing leg body respective-portion acceleration calculating means 33. Further, the joint reaction force $^T(F_1x, F_1z)$ acting on the ankle portion 12 at the tip portion of the crus portion 11 is approximately equal to the estimated value of the floor reaction force derived by the foregoing floor reaction force estimating means 36 for the leg body 2 having the crus portion 11. More specifically, in the single stance state, when the leg body 2 is on the ground, the joint reaction force $^T(F_1x, F_1z)$ is the floor reaction force $^T(Fx, Fz)$ derived by the foregoing equation (2) and, when the leg body 2 is the free-leg side leg body, $^T(F_1x, F_1z) = {}^T(0, 0)$. On the other hand, in the double stance state, when the leg body 2 is the leg body on the rear side of the human being 1 facing forward in the advancing direction, the joint reaction force $^T(F_1x, F_1z)$ is the floor reaction force $^T(Frx, Frz)$ of the foregoing equations (5) and, when the leg body 2 is the front-side leg body, it is the floor reaction force $^T(Ffx, Ffz)$ of the foregoing equations (5).

Therefore, the joint reaction force $^T(F_2x, F_2z)$ acting on the knee joint 10 of each leg body 2 is derived from data about the acceleration $^T(a_2x, a_2z)$ of the center of gravity G2 of the crus portion 11 derived by the leg body respective-portion acceleration calculating means 33, data about the floor reaction force $(= {}^T(F_1x, F_1z))$ derived by the floor reaction force estimating means 36, data about the weight $m_2$ of the crus portion 11 derived in advance, and a value of the acceleration of gravity g, using the foregoing equation (10).

Further, referring to FIG. 11, it is given that a moment acting on the ankle portion 12 at the tip portion of the crus portion 11 is $M_1$, a moment acting on the portion of the knee joint 10 of the crus portion 11 is $M_2$, a moment of inertia about the center of gravity G2 of the crus portion 11 is $I_{G2}$, and an angular velocity about the center of gravity G2 of the crus portion 11 is $\alpha_2$. Further, given that, in correspondence with the foregoing FIG. 4, a distance between the center of gravity G2 of the crus portion 11 and the center of the knee joint 10 is $t_2$, and a distance between the center of gravity G2 of the crus portion 11 and the ankle portion 12 is $t_2'$ (=Ld−$t_2$), an equation of motion for the rotating motion about the center of gravity G2 of the crus portion 11 becomes the following equation (11).

$$I_{G2} \cdot \alpha_2 = M_1 - M_2 + F_1x \cdot t_2' \cdot \cos\theta d - F_1z \cdot t_2' \cdot \sin\theta d + \quad (11)$$
$$F_2x \cdot t_2 \cdot \cos\theta d - F_2z \cdot t_2 \cdot \sin\theta d$$

therefore, $$M_2 = M_1 - I_{G2} \cdot \alpha_2 + F_1x \cdot t_2' \cdot \cos\theta d - F_1z \cdot t_2' \cdot \sin\theta d +$$
$$F_2x \cdot t_2 \cdot \cos\theta d - F_2z \cdot t_2 \cdot \sin\theta d$$

Here, $M_1$ in the equation (11) is a moment obtained as the outer product (vector product) of a floor reaction force acting point vector derived by the foregoing floor reaction force acting point estimating means 35 with respect to the leg body 2 having the crus portion 11 relating to the equation (11), and a floor reaction force vector derived by the foregoing floor reaction force estimating means 36 with respect to that leg body 2. $\alpha_2$ is an angular velocity of the crus portion 11 derived by the foregoing leg body respective-portion angular velocity calculating means 34. $\theta d$ is an inclination angle of the crus portion 11 derived by the foregoing leg body posture calculating means 28. $^T(F_1x, F_1z)$ is, as described before, the estimated value of the floor reaction force derived by the floor reaction force estimating means 36. Further, $^T(F_2x, F_2z)$ is derived by the foregoing equation (10). The moment of inertia $I_{G2}$ is derived in advance and stored in the arithmetic processing unit 16 along with data about the weight $m_2$ and size of the crus portion 11, and so forth.

Therefore, the moment $M_2$ acting on the knee joint 10 is derived from data about the estimated value of the floor reaction force by the floor reaction force estimating means 36, data about the floor reaction force acting point vector by the floor reaction force acting point estimating means 35, data about the angular velocity $\alpha_2$ of the crus portion 11 by the leg body respective-portion angular velocity calculating means 34, data about the inclination angle $\theta d$ of the crus portion 11 by the leg body posture calculating means 28, data about the joint reaction force $^T(F_2x, F_2z)$ derived by the foregoing equation (10), and data about the moment of inertia $I_{G2}$, the size (Ld), and the position ($t_2$) of the center of gravity G2 of the crus portion 11 derived in advance, using the foregoing equation (11).

After deriving the moment $M_2$ acting on the portion of the knee joint 10 of the crus portion 11 as described above, the joint moment estimating means 37 derives, according to the processing like the processing of calculation thereof, a moment acting on the portion of the hip joint 8 of the thigh portion 9. The basic idea of this processing is the same as the technique of deriving the moment $M_2$ of the knee joint 10, and therefore, detailed showing and explanation are omitted. An outline thereof is as follows.

Specifically, at the outset, a joint reaction force $^T(F_3x, F_3z)$ acting on the portion of the hip joint 8 of the thigh portion 9 is derived using the following equation (12) (an equation in the same form as the foregoing equation (10)) based on an equation of motion for the translation motion of the center of gravity G1 (see FIG. 4) of the thigh portion 9.

$$^T(F_3x, F_3z) = {}^T(F_2x - m_1 \cdot a_1x, F_2z - m_1 \cdot a_1z - m_1 \cdot g) \quad (12)$$

Here, $^T(F_2x, F_2z)$ is the joint reaction force of the knee joint 10 derived before by the foregoing equation (10). $^T(a_1x, a_1z)$ is an acceleration (translation acceleration) of the center of gravity G1 of the thigh portion 9 in the absolute coordinate system Cf, which is derived by the foregoing leg body respective-portion acceleration calculating means 33. Further, $m_1$ is the weight of the thigh portion 9 derived in advance, and g is the acceleration of gravity.

Then, a moment $M_3$ acting on the portion of the hip joint 8 of the thigh portion 9 is derived using the following equation (13) (an equation in the same form as the foregoing equation (11)) based on an equation of motion for the rotating motion about the center of gravity G1 of the thigh portion 9.

$$M_3 = M_2 - I_{G1} \cdot \alpha_1 + F_2x \cdot t_1' \cdot \cos\theta c - F_2z \cdot t_1' \cdot \sin\theta c + \quad (13)$$
$$F_3x \cdot t_1 \cdot \cos\theta c - F_3z \cdot t_1 \cdot \sin\theta c$$

Here, $M_2$ is the moment on the knee joint 10 derived by the foregoing equation (11), $^T(F_2x, F_2z)$ is the joint reaction force on the knee joint 10 derived by the foregoing equation (10), $^T(F_3x, F_3z)$ is the joint reaction force on the hip joint 8 derived by the foregoing equation (12), $I_{G1}$ is a moment of inertia about the center of gravity G1 of the thigh portion 9 derived in advance, $α_1$ is an angular velocity of the thigh portion 9 derived by the foregoing leg body respective-portion angular velocity calculating means 34, and θc is an inclination angle of the thigh portion 9 derived by the foregoing leg body posture calculating means 28. Further, $t_1$ is a distance from the center of the hip joint 8 to the center of gravity G1 of the thigh portion 9 (see FIG. 4), and $t_1'$ is a distance from the center of the knee joint 10 to the center of gravity G1 of the thigh portion 9 (Lc–$t_1$ in FIG. 4), which are determined based on the position of the center of gravity G1 and the size (length) of the thigh portion 9 derived in advance.

The processing described above is successively executed per cycle time of the foregoing arithmetic processing unit 16, so that the floor reaction force acting on each leg body 2, and the moments acting on the knee joint 10 and the hip joint 8 of each leg body 2 are sequentially estimated in real time.

Although detailed explanation is omitted in this specification, the derived estimated values of the moments on the knee joints 10 and the hip joints 8 are used for a control of, for example, a device assisting walking of the human being 1 (a device including electric motors or the like that can give auxiliary torques to the knee joints 10 and the hip joints 8).

Figure 12:
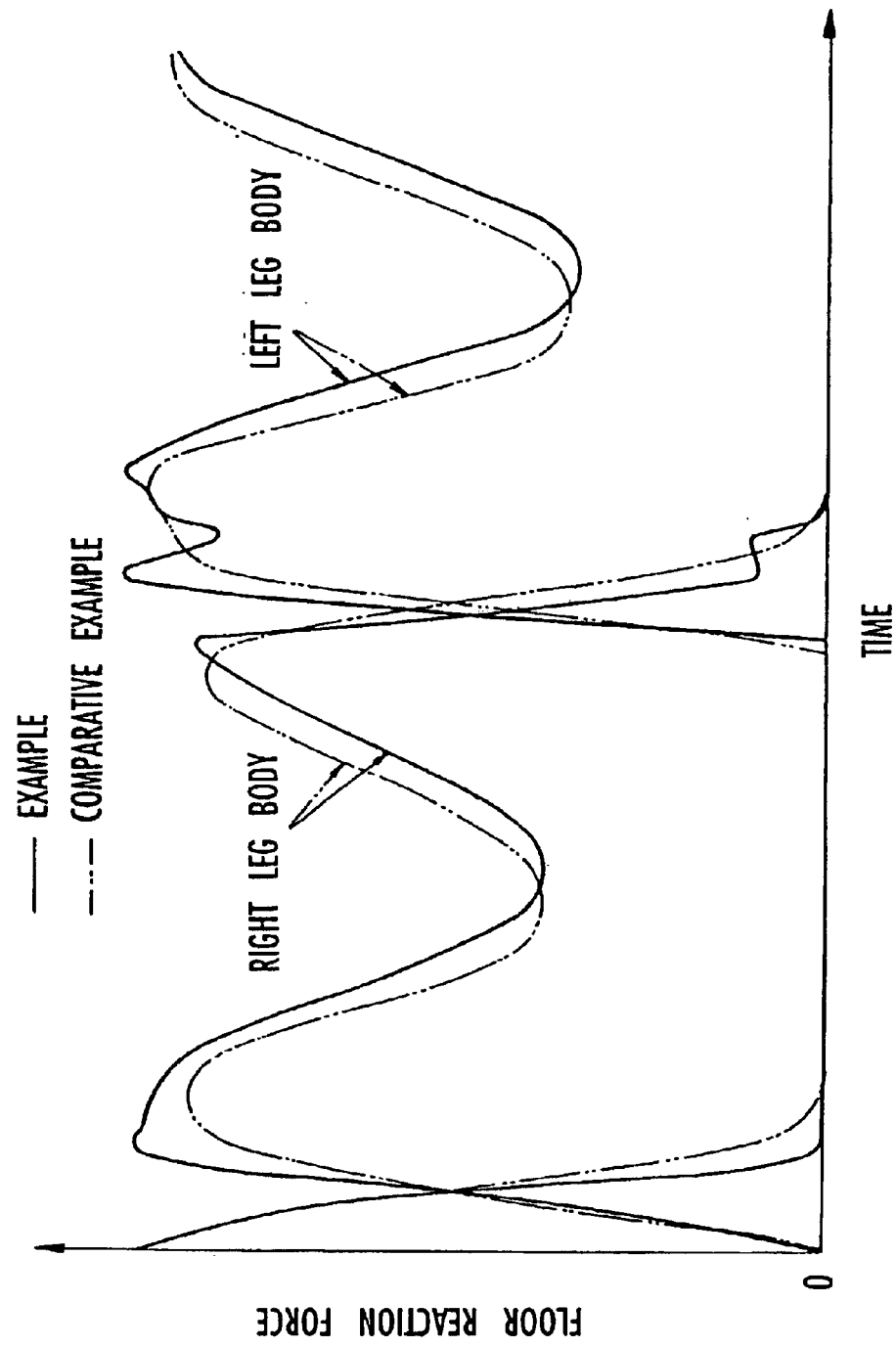
FIG. 12 is a graph illustrating the states of temporal variations of estimated values of floor reaction forces during normal walking, which are derived by the embodiment of the present invention.
Figure 13:
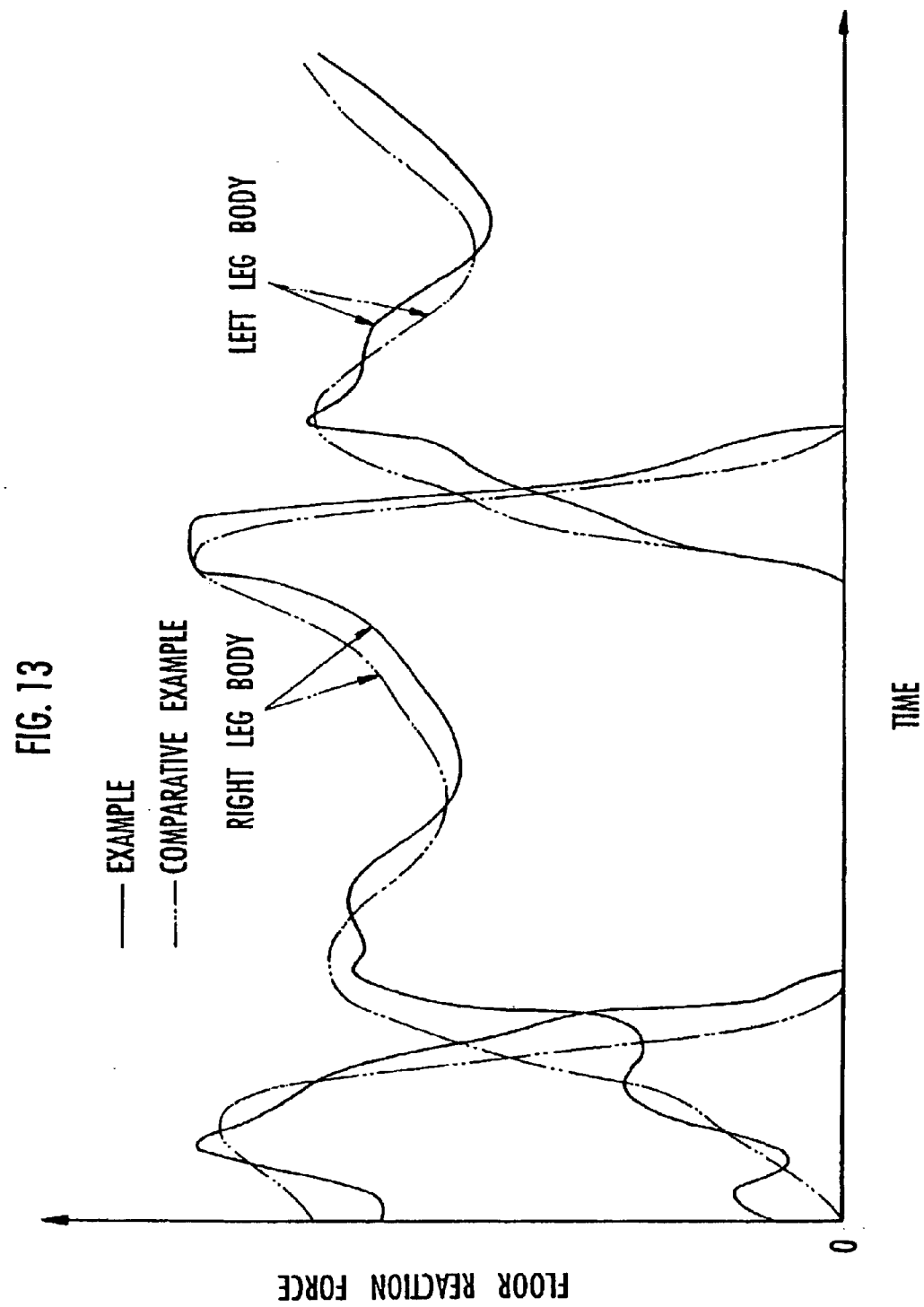
FIG. 13 is a graph illustrating the states of temporal variations of estimated values of floor reaction forces upon going upstairs, which are derived by the embodiment of the present invention.
Figure 14:
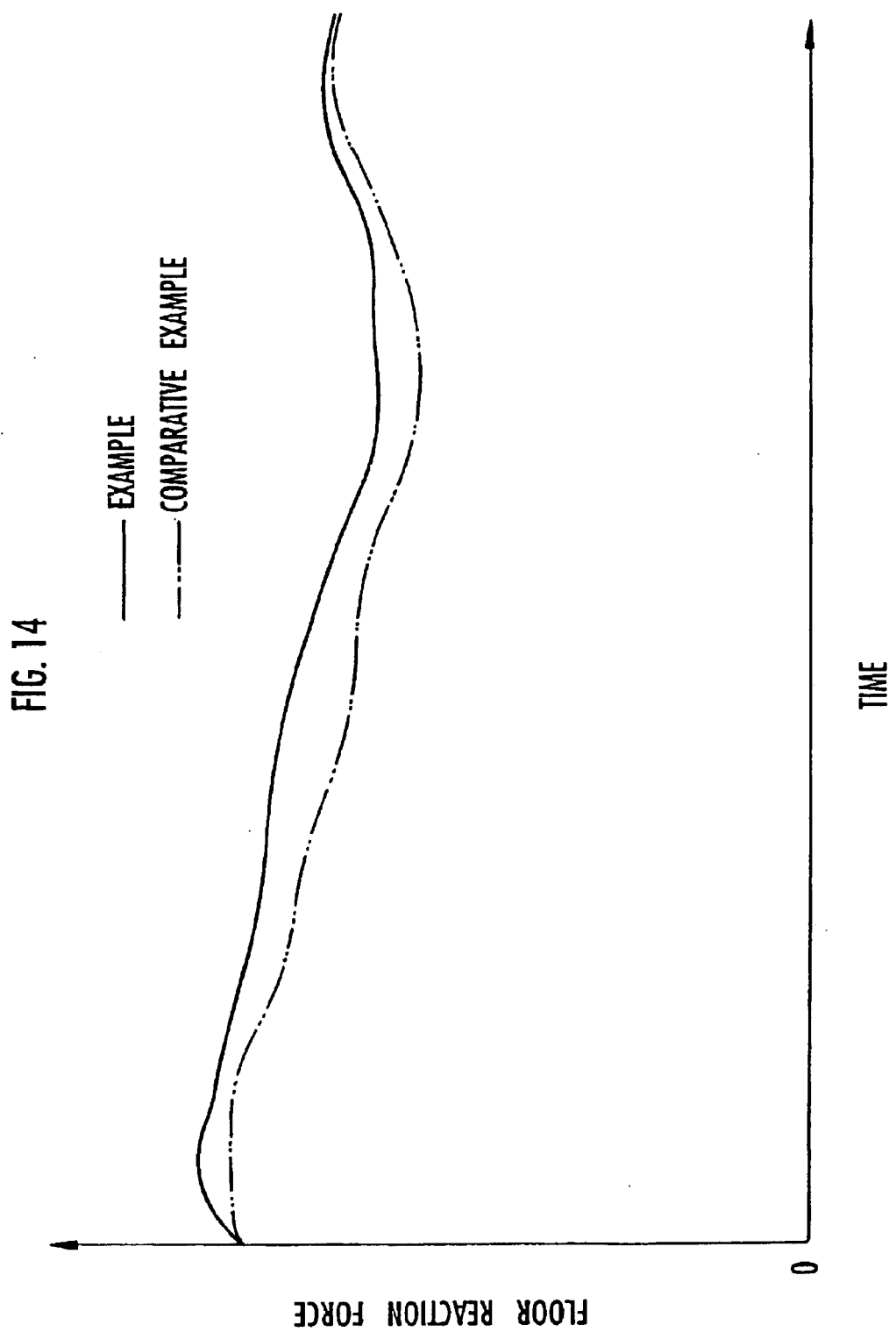
FIG. 14 is a graph illustrating the state of temporal variation of estimated values of floor reaction forces upon standing up from a chair, which are derived by the embodiment of the present invention.
Figure 15:
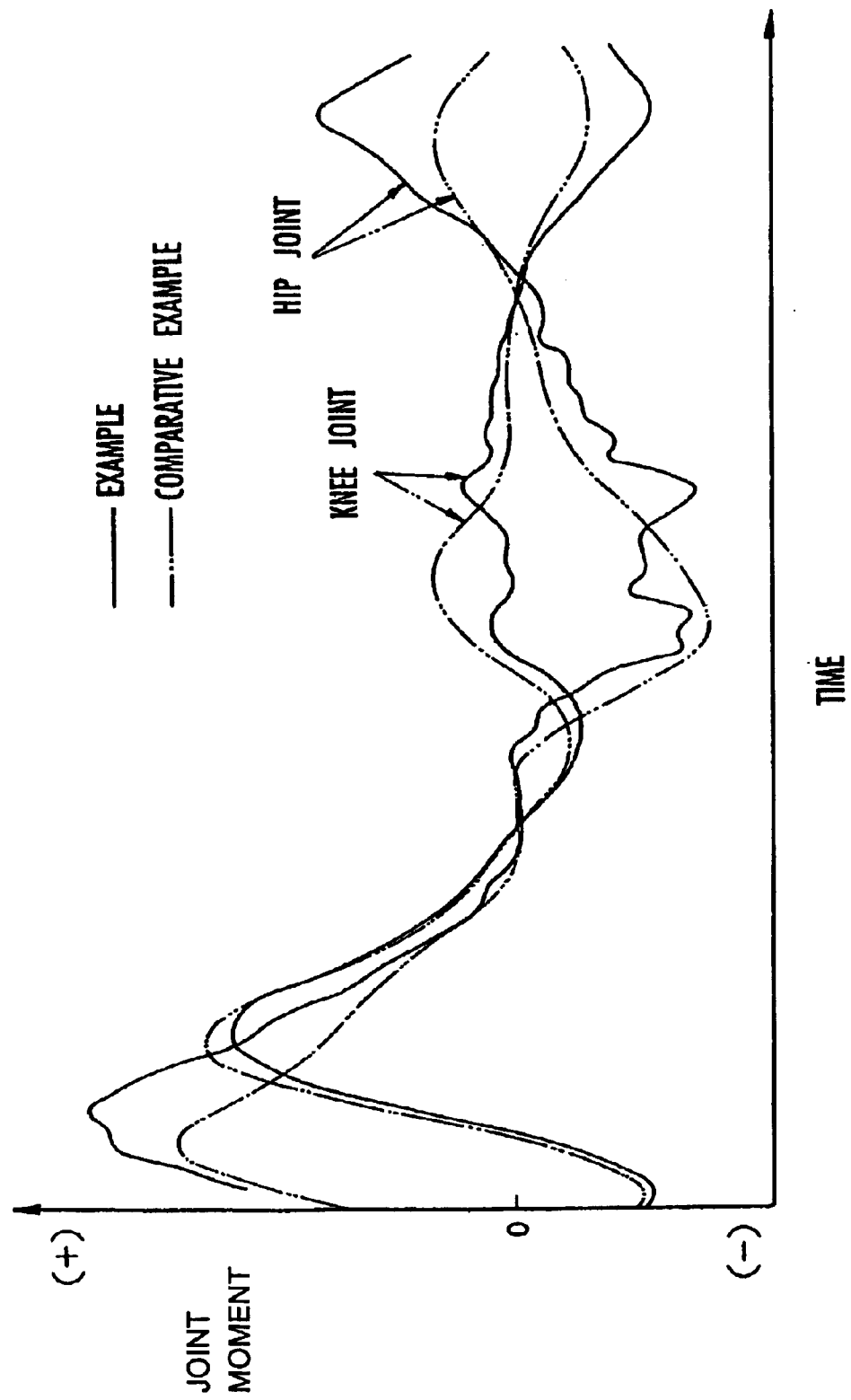
FIG. 15 is a graph illustrating the states of temporal variations of estimated values of moments on a knee joint and a hip joint, which are derived by the embodiment of the present invention.

The states of temporal variations of estimated values of floor reaction forces (specifically, absolute values of the estimated values of the floor reaction forces) derived by the foregoing processing of the arithmetic processing unit 16 are illustrated in FIGS. 12 to 14 by solid lines. Further, the states of temporal variations of estimated values of moments on the knee joint 10 and the hip joint 8 derived by the processing of the arithmetic processing unit 16 are illustrated in FIG. 15 by solid lines. Here, FIGS. 12 and 15 are illustration wherein the human being 1 walks on a flatland at a substantially constant speed, FIG. 13 is illustration wherein the human being 1 walks upstairs, and FIG. 14 is illustration wherein the human being 1 stands up from the state of sitting in a chair. In FIGS. 12 to 14, comparative examples (corresponding to true values of floor reaction forces) obtained by actually measuring floor reaction forces using a force meter or the like are also shown by imaginary lines. Further, in FIG. 15, comparative examples (corresponding to true values of moments on the knee joint 10 and the hip joint 8) obtained by actually measuring moments on the knee joint 10 and the hip joint 8 using a torque meter or the like are also shown by imaginary lines.

As is clear by referring to FIGS. 12 to 14, it is understood that, according to the present embodiment, the accurate estimated values of the floor reaction forces are obtained irrespective of the motion type or motion environment of the leg bodies 2. Further, in the present embodiment, as shown in FIG. 15, the moments on the knee joint 10 and the hip joint 8 can also be estimated with relatively high accuracy using the estimated values of the floor reaction forces.

As described above, according to this embodiment, it is possible to easily estimate in real time the floor reaction force acting on each leg body 2 and the moments acting on the hip joint 8 and the knee joint 10 of each leg body 2 using relatively small and light sensors such as the angle sensors 22 and 23 respectively attached to the hip joints 8 and the knee joints 10, and the gyro sensors 14 and 19 and the accelerometers 15, 20, and 21 attached to the body 5, without attaching such sensors to the leg bodies 2 that become obstructive to the walking of the human being 1, or apply loads to the motion of the leg bodies 2. Moreover, such estimation can be carried out with relatively high accuracy irrespective of the motion type or motion environment of the leg bodies 2, i.e. whether it is walking on a flatland, walking on the stairs, or the like.

In the embodiment described above, the description has been given about the case, as an example, wherein the present invention is applied to the human being 1. However, the present invention is also applicable to a bipedal walking robot as a bipedal walking moving body. Here, in case of the bipedal walking robot, it may have a structure where a waist and a chest are integral with each other. In this case, it is possible to attach the gyro sensor and the forward/backward accelerometer to either one of the waist and the chest, and estimate floor reaction forces and moments on joints of leg bodies in the same manner as in the present embodiment. Further, in case of the bipedal walking robot, it is also possible grasp bending angles of hip joints and knee joints based on control amounts of a controller for actuators of those joints.

In the foregoing embodiment, the detection data of the waist upward/downward accelerometer 21 is uses as it is for judging the motion state of the leg bodies 2. However, instead of such detection data, it is possible to use, for example, values of components of the acceleration $a_0$ of the waist 3 in the vertical direction (Z-axis direction) in the absolute coordinate system Cf, which are derived by the foregoing reference acceleration measuring means 27.

Industrial Applicability

As described above, the present invention is useful in that, when performing walking assistance or walking control of a bipedal walking moving body such as a human being or a robot, floor reaction forces and joint moments acting on leg bodies of the moving body can be grasped.

What is claimed is:

1. A method of estimating a floor reaction force acting on each of leg bodies of a bipedal walking moving body, comprising:

a first step of judging whether a motion state of the leg bodies of said bipedal walking moving body is a single stance state in which only one of the leg bodies touches the ground, or a double stance state in which both leg bodies touch the ground;

a second step of sequentially deriving positions of the center of gravity of said bipedal walking moving body, and sequentially deriving accelerations of said center of gravity in an absolute coordinate system fixed relative to the ground by the use of time series data about the positions of said center of gravity;

a third step of sequentially deriving positions of a specific portion relative to said center of gravity at least in said double stance state, said specific portion predetermined in the neighborhood of a lower end portion of each leg body;

a step of deriving estimated values of said floor reaction force acting on the leg body touching the ground sequentially, in the single stance state of said bipedal walking moving body, based on an equation of motion for said center of gravity expressed by a weight and an acceleration of gravity of the bipedal walking moving body, the acceleration of said center of gravity, and said floor reaction force acting on the leg body touching the ground;

and a step of deriving estimated values of said floor reaction forces respectively acting on both leg bodies sequentially, in the double stance state of said bipedal walking moving body, based on an equation of motion for said center of gravity expressed by a weight and an acceleration of gravity of the bipedal walking moving body, the acceleration of said center of gravity, and said floor reaction forces respectively acting on both leg bodies, and an expression of relation between the position of said specific portion of each leg body relative to said center of gravity and said floor reaction force acting on said leg body, said expression of relation being determined based on assumption that said floor reaction force acting on each leg body acts from said specific portion of said leg body toward said center of gravity.

2. A method according to claim 1, wherein said specific portion of each leg body is an ankle portion of said leg body.

3. A method according to claim 1, further comprising a step of measuring an acceleration, in an upward/downward direction, of a lower portion of a body supported on both leg bodies via a hip joint of each leg body, said lower portion of the body located near said hip joints, wherein, in said first step, the motion state of said bipedal walking moving body is judged such that when the acceleration of said lower portion of the body in the upward/downward direction increases to a predetermined threshold value or more, said double stance state starts while said single stance state finishes and, when the estimated value of said floor reaction force acting on the leg body which precedingly makes a takeoff is lowered to a predetermined threshold value or less in said double stance state, said double stance state finishes while said single stance state starts.

4. A method according to claim 1, further comprising a step of respectively measuring an inclination angle of a body supported on both leg bodies via a hip joint of each leg body, bending angles respectively of at least the hip joint and a knee joint of each leg body, and an acceleration of a predetermined reference point of said bipedal walking moving body in said absolute coordinate system, wherein, in said second step, based on the inclination angle of said body, the bending angles respectively of said hip joints and said knee joints, a rigid body link model formed by expressing said bipedal walking moving body as a linked body of a plurality of rigid bodies, prederived weights of respective rigid-body corresponding portions of the bipedal walking moving body corresponding to the respective rigid bodies of said rigid body link model, and positions of the prederived centers of gravity of the rigid-body corresponding portions in the respective rigid-body corresponding portions, positions of the center of gravity of said bipedal walking moving body relative to said reference point are sequentially derived, accelerations of said center of gravity relative to said reference point are sequentially derived based on time series data about the positions of said center of gravity, and the acceleration of said center of gravity in said absolute coordinate system is derived from the acceleration of said center of gravity relative to said reference point, and the acceleration of said reference point in said absolute coordinate system.

5. A method according to claim 4, wherein said reference point is set to said body.

6. A method according to claim 4, wherein said body has a waist coupled to both leg bodies via the hip joints, and a chest located on said waist so as to be tiltable relative to said waist, and the inclination angle of said body used for deriving the position of said center of gravity comprises inclination angles respectively of said waist and said chest.

7. A method according to claim 6, wherein said rigid body link model is a model expressing a crus portion located on a lower side of the knee joint of each leg body of said bipedal walking moving body, a thigh portion between said knee joint and said hip joint, said waist, and an upper body portion located on an upper side of said waist and including said chest, as rigid bodies, respectively.

8. A method of estimating a moment acting on at least one joint of each leg body of the bipedal walking moving body by the use of the estimated values of the floor reaction force on each leg body sequentially derived by the method according to claim 1, comprising:

a step of respectively measuring an inclination angle of a body supported on both leg bodies via a hip joint of each leg body, bending angles respectively of at least the hip joint and a knee joint of each leg body, and an acceleration of a predetermined reference point of said bipedal walking moving body in said absolute coordinate system;

a step of sequentially deriving inclination angles of respective rigid-body corresponding portions of the bipedal walking moving body corresponding to the respective rigid bodies of said rigid body link model, based on the inclination angle of said body, the bending angles respectively of said hip joint and said knee joint of each leg body, and a rigid body link model formed by expressing said bipedal walking moving body as a linked body of a plurality of rigid bodies;

a step of sequentially deriving positions of the centers of gravity of the respective rigid-body corresponding portions relative to said reference point, based on the inclination angles of said respective rigid-body corresponding portions, prederived weights of the respective rigid-body corresponding portions, and positions of the prederived centers of gravity of the rigid-body corresponding portions in the respective rigid-body corresponding portions, and sequentially deriving accelerations of the centers of gravity of the respective rigid-body corresponding portions relative to said reference point based on time series data about the positions of the centers of gravity of the respective rigid-body corresponding portions;

a step of sequentially deriving accelerations of the centers of gravity of the respective rigid-body corresponding portions in said absolute coordinate system from the accelerations of the centers of gravity of the respective rigid-body corresponding portions relative to said reference point, and the accelerations of said reference point in said absolute coordinate system;

a step of sequentially deriving angular velocities of the respective rigid-body corresponding portions based on time series data about the inclination angles of the respective rigid-body corresponding portions;

a step of sequentially deriving estimated positions of a floor reaction force acting point of each leg body in said bipedal walking moving body, based on at least one of an inclination angle of a thigh portion of said leg body and the bending angle of the knee joint of said leg body as the rigid-body corresponding portions of said bipedal walking moving body; and a step of estimating a moment acting on at least one of the joints of each leg body of said bipedal walking moving body based on an inverse dynamics model using the estimated value of said floor reaction force, the estimated position of said floor reaction force acting point, the accelerations of the centers of gravity of the respective rigid-body corresponding portions and the angular velocities of said rigid-body corresponding portions in said absolute coordinate system, the inclination angles of the respective rigid-body corresponding portions, the prederived weights and sizes of the respective rigid-body corresponding portions, the positions of the prederived centers of gravity of the rigid-body corresponding portions in the respective rigid-body corresponding portions, and prederived moments of inertia of the respective rigid-body corresponding portions.

9. A method of estimating a moment acting on at least one joint of each leg body of the bipedal walking moving body by the use of the estimated values of the floor reaction force on each leg body sequentially derived by the method according to claim 4, comprising:

a step of sequentially deriving inclination angles, in said absolute coordinate system, of the respective rigid-body corresponding portions of the bipedal walking moving body corresponding to the respective rigid bodies of said rigid body link model, based on the inclination angle of said body, the bending angles respectively of said hip joint and said knee joint of each leg body, and said rigid body link model;

a step of sequentially deriving positions of the centers of gravity of the respective rigid-body corresponding portions relative to said reference point, based on the inclination angles of said respective rigid-body corresponding portions, the prederived weights of the respective rigid-body corresponding portions, and the positions of the centers of gravity of the rigid-body corresponding portions in the respective rigid-body corresponding portions, and sequentially deriving accelerations of the centers of gravity of the respective rigid-body corresponding portions relative to said reference point based on time series data about the positions of the centers of gravity of the respective rigid-body corresponding portions;

a step of sequentially deriving accelerations of the centers of gravity of the respective rigid-body corresponding portions in said absolute coordinate system from the accelerations of the centers of gravity of the respective rigid-body corresponding portions relative to said reference point, and the accelerations of said reference point in said absolute coordinate system;

a step of sequentially deriving angular velocities of the respective rigid-body corresponding portions based on time series data about the inclination angles of the respective rigid-body corresponding portions;

a step of sequentially deriving estimated positions of a floor reaction force acting point of each leg body in said bipedal walking moving body, based on at least one of an inclination angle of a thigh portion of said leg body and the bending angle of the knee joint of said leg body as the rigid-body corresponding portions of said bipedal walking moving body; and a step of estimating a moment acting on at least one of the joints of each leg body of said bipedal walking moving body based on an inverse dynamics model using the estimated value of said floor reaction force, the estimated position of said floor reaction force acting point, the accelerations of the centers of gravity of the respective rigid-body corresponding portions and the angular velocities of said rigid-body corresponding portions in said absolute coordinate system, the inclination angles of the respective rigid-body corresponding portions, the prederived weights and sizes of the respective rigid-body corresponding portions, the positions of the prederived centers of gravity of the rigid-body corresponding portions in the respective rigid-body corresponding portions, and prederived moments of inertia of the respective rigid-body corresponding portions.

* * * * *